United States Patent
Hodoshima et al.

(10) Patent No.: US 10,549,267 B2
(45) Date of Patent: *Feb. 4, 2020

(54) ZEOLITE CATALYSTS, METHODS FOR PRODUCING ZEOLITE CATALYSTS, AND METHODS FOR PRODUCING LOWER OLEFINS

(71) Applicant: CHIYODA CORPORATION, Yokohama-shi, Kanagawa (JP)

(72) Inventors: Shinya Hodoshima, Yokohama (JP); Fuyuki Yagi, Yokohama (JP); Azusa Motomiya, Yokohama (JP); Shuhei Wakamatsu, Yokohama (JP); Sachio Asaoka, Yokohama (JP)

(73) Assignee: CHIYODA CORPORATION, Yokohama-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/402,506

(22) Filed: May 3, 2019

(65) Prior Publication Data

US 2019/0255516 A1 Aug. 22, 2019

Related U.S. Application Data

(60) Division of application No. 15/626,733, filed on Jun. 19, 2017, now abandoned, which is a continuation of application No. 14/416,998, filed as application No. PCT/JP2013/065811 on Jun. 7, 2013, now Pat. No. 9,821,301.

(30) Foreign Application Priority Data

Jul. 26, 2012 (JP) ................. 2012-165754

(51) Int. Cl.
| | |
|---|---|
| C07C 4/06 | (2006.01) |
| B01J 29/88 | (2006.01) |
| B01J 29/40 | (2006.01) |
| C01B 39/06 | (2006.01) |
| C07C 11/06 | (2006.01) |
| B01J 29/46 | (2006.01) |
| C01B 39/46 | (2006.01) |
| B01J 29/87 | (2006.01) |
| B01J 37/00 | (2006.01) |
| C10G 11/05 | (2006.01) |
| C01B 39/36 | (2006.01) |
| B01J 35/02 | (2006.01) |
| B01J 37/10 | (2006.01) |

(52) U.S. Cl.
CPC ............. *B01J 29/88* (2013.01); *B01J 29/40* (2013.01); *B01J 29/405* (2013.01); *B01J 29/46* (2013.01); *B01J 29/87* (2013.01); *B01J 35/023* (2013.01); *B01J 37/0009* (2013.01); *B01J 37/10* (2013.01); *C01B 39/065* (2013.01); *C01B 39/36* (2013.01); *C01B 39/46* (2013.01); *C07C 4/06* (2013.01); *C07C 11/06* (2013.01); *C10G 11/05* (2013.01); *B01J 2229/18* (2013.01); *B01J 2229/186* (2013.01); *B01J 2229/20* (2013.01); *B01J 2229/42* (2013.01); *C07C 2529/42* (2013.01); *C07C 2529/88* (2013.01); *C07C 2529/89* (2013.01); *C10G 2400/20* (2013.01); *Y02P 20/52* (2015.11)

(58) Field of Classification Search
CPC ....... C10G 11/05; C10G 2400/20; C07C 4/06; C07C 11/06; C07C 2529/88; C07C 2529/89; C07C 2529/42
USPC ................. 585/648, 653; 208/113, 118, 119, 208/120.01, 121, 124
See application file for complete search history.

(56) References Cited

U.S. PATENT DOCUMENTS

| | | |
|---|---|---|
| 4,605,805 A | 8/1986 | Chang et al. |
| 5,013,537 A | 5/1991 | Patarin et al. |
| 5,182,242 A | 1/1993 | Marler |
| 5,231,187 A | 7/1993 | Beshty et al. |
| 6,051,205 A | 4/2000 | Yamamoto et al. |
| 6,414,197 B1 | 7/2002 | Kustov et al. |
| 7,074,734 B2 | 7/2006 | Vu et al. |
| 7,186,872 B2 | 3/2007 | Juttu et al. |
| 7,393,990 B2 | 7/2008 | Xu et al. |
| 2003/0018231 A1 | 1/2003 | Xu et al. |
| 2006/0002849 A1 | 1/2006 | Vitale-Rojas et al. |
| 2006/0058562 A1 | 3/2006 | Choi et al. |
| 2010/0322847 A1 | 12/2010 | Xiao et al. |
| 2013/0045860 A1 | 2/2013 | Xiao |
| 2013/0123096 A1 | 5/2013 | Xiao et al. |
| 2013/0149225 A1 | 6/2013 | Schwefer et al. |

FOREIGN PATENT DOCUMENTS

| | | |
|---|---|---|
| JP | 02-010760 Y2 | 3/1990 |
| JP | 05-117256 A | 5/1993 |

(Continued)

OTHER PUBLICATIONS

Machine Translation of JP 06-330055, Nov. 23, 2016, pp. 1-11.*

(Continued)

*Primary Examiner* — Elizabeth D Wood
(74) *Attorney, Agent, or Firm* — Westerman, Hattori, Daniels & Adrian, LLP

(57) ABSTRACT

Provided are zeolite catalysts that allow reactions to proceed at temperatures as low as possible when lower olefins are produced from hydrocarbon feedstocks with low boiling points such as light naphtha, make it possible to make propylene yield higher than ethylene yield in the production of lower olefins, and have long lifetime. The zeolite catalysts are used in the production of lower olefins from hydrocarbon feedstocks with low boiling points such as light naphtha. The zeolite catalysts are MFI-type crystalline aluminosilicates containing iron atoms and have molar ratios of iron atoms to total moles of iron atoms and aluminum atoms in the range from 0.4 to 0.7. The use of the zeolite catalysts make it possible to increase propylene yield, to lower reaction temperatures, and to extend catalyst lifetime.

3 Claims, 3 Drawing Sheets

(56) References Cited

FOREIGN PATENT DOCUMENTS

| | | |
|---|---|---|
| JP | 06-199707 A | 7/1994 |
| JP | 06-330055 A | 11/1994 |
| JP | 07-507485 A | 8/1995 |
| JP | 2002-294254 A | 10/2002 |
| JP | 2007-106739 A | 4/2007 |
| JP | 2008-512236 A | 4/2008 |
| WO | 93/24226 A1 | 12/1993 |

OTHER PUBLICATIONS

International Search Report dated Aug. 20, 2013, issued in counterpart International patent application No. PCT/JP2013/065811 (in English; 2 pages).

Hodoshima, Shinya et al., "Production of Propylene from Naphtha Using MFI-Zeolite/Metal-Oxide Composite Catalyst", Abstract of Annual Meeting of the Society of Chemical Engineers, Japan, Feb. 17, 2013, vol. 78, SCEJ 78th Annual Meeting (Osaka, 2013) (w/ English translation; 5 pages).

Office Action dated May 30, 2017 in Japanese patent application 2016-175400 counterpart to U.S. Appl. No. 15/626,733 (w/ English translation; 7 pages).

\* cited by examiner

[FIG. 1]
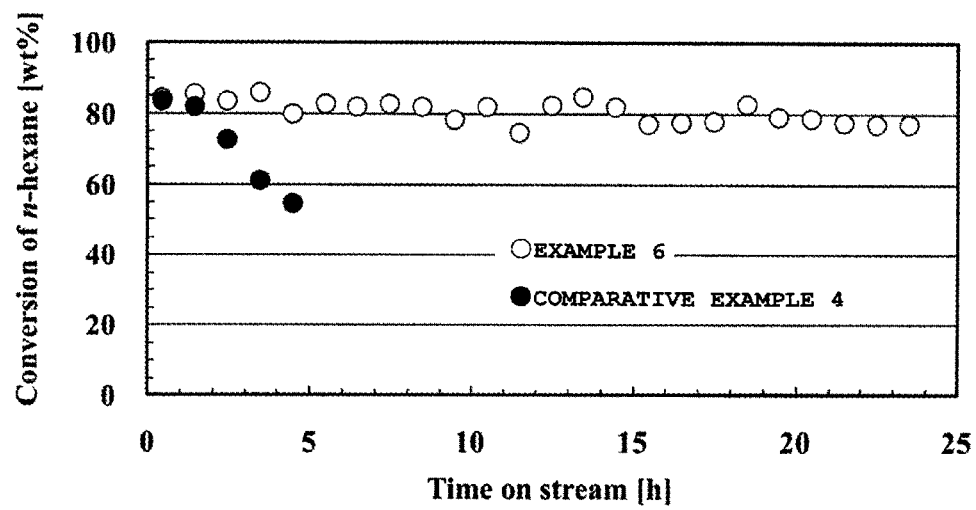
Time courses of feedstock conversions in catalytic cracking of n-hexane with FeGaAl-MFI/$Al_2O_3$ catalysts (Example 6 and Comparative example 4)

[FIG. 2]
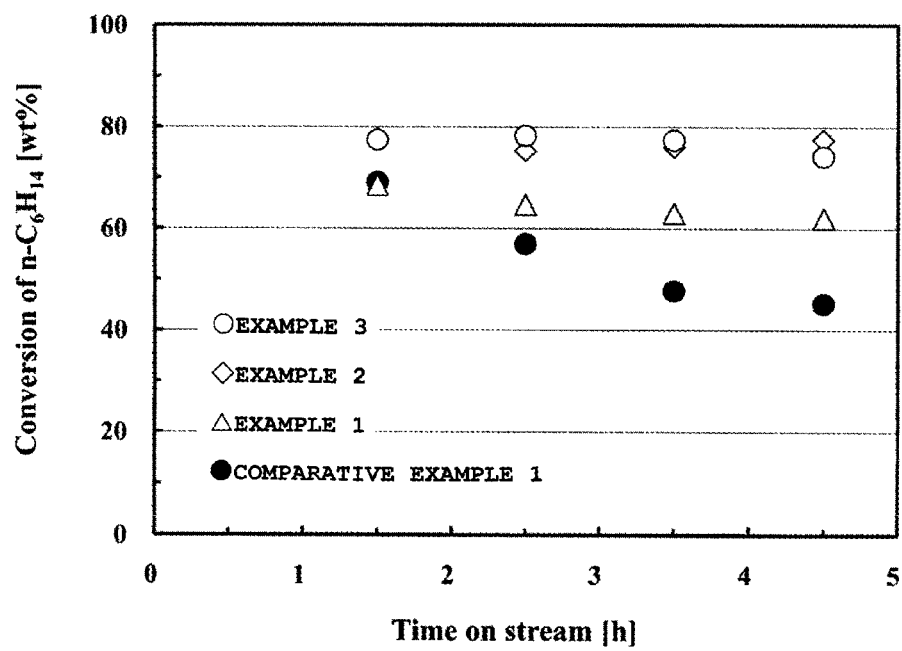
Time courses of feedstock conversions in catalytic cracking of n-hexane with various MFI-Zeolite/Al$_2$O$_3$ catalysts

[FIG. 3]
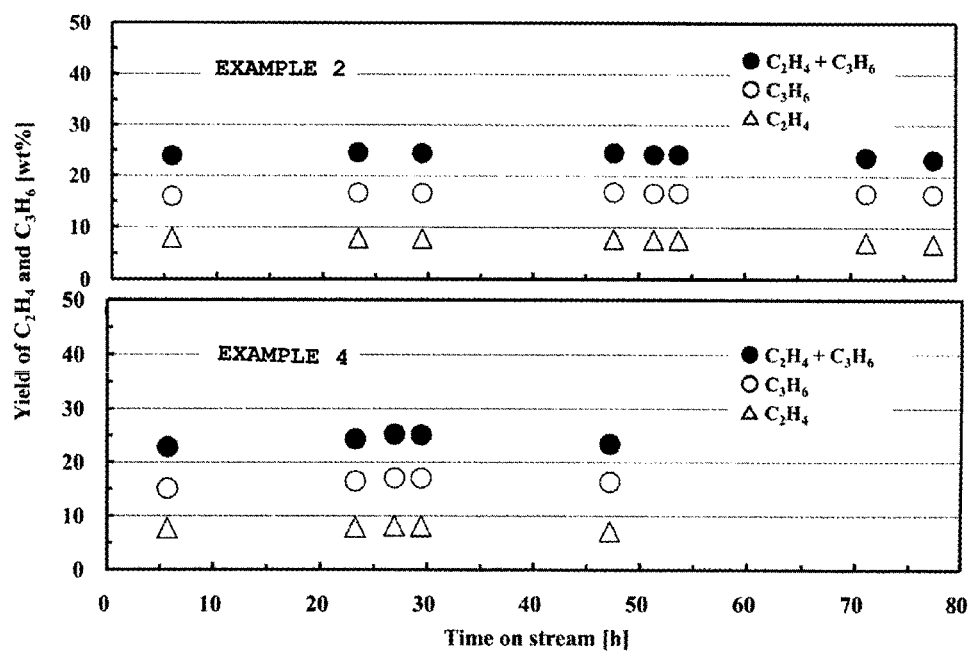
Time courses of yields of lower olefins in catalytic cracking of n-hexane with FeGaAl-MFI/Al$_2$O$_3$ catalyst (Example 2) and FeAl-MFI/Al$_2$O$_3$ catalyst (Example 4)

ZEOLITE CATALYSTS, METHODS FOR PRODUCING ZEOLITE CATALYSTS, AND METHODS FOR PRODUCING LOWER OLEFINS

CROSS REFERENCE

This Application is a divisional of U.S. application Ser. No. 15/626,733 filed on Jun. 19, 2017, now abandoned which is a continuation of U.S. application Ser. No. 14/416,998 filed on Jan. 23, 2015, and now U.S. Pat. No. 9,821,301 which is a U.S. national stage of International Application No. PCT/JP2013/065811 filed on Jun. 7, 2013, each of which claims benefit of Japanese Patent Application No. 2012-165754, filed on Jul. 26, 2012, the entire contents of each of the foregoing are herein incorporated by reference.

TECHNICAL FIELD

The present invention relates to zeolite catalysts for producing lower olefins from hydrocarbons with low boiling points such as light naphtha. The invention also relates to methods for producing these zeolite catalysts and to methods for producing lower olefins with these zeolite catalysts.

BACKGROUND ART

Lower olefins (e.g., ethylene and propylene) are important basic raw materials in the petrochemical industries and demand for lower olefins is expected to be steadily increased in the coming years. At present, lower olefins have been produced mainly by steam cracking of naphtha. However, this process, which is non-catalytic, requires high temperatures between 800° C. and 900° C. for cracking, resulting in a large amount of energy consumption.

In this technique, the main product is ethylene, while propylene is a by-product (the gravimetric ratios of ethylene to propylene are ca. 2.0). Therefore, propylene supply by this technique might be insufficient due to the expansion of propylene demand. From these viewpoints, an energy-saving alternative process for producing propylene with high yield from the naphtha feedstock has been intensively desired.

Recently, research and development has been actively conducted for catalytic cracking processes of naphtha using zeolite-based solid acid catalysts, typified by ZSM-5 (Al-MFI zeolite).

For example, it has been proposed that a zeolite-based solid acid catalyst be produced by a process including subjecting a mixture of raw materials containing ZSM-5, a layered compound such as bentonite, silicon dioxide, phosphorus pentoxide, aluminum oxide, and boron oxide, to a crosslinking reaction in water to form an aqueous slurry containing a crosslinked product, and then forming the aqueous slurry into pellets as a solid acid catalyst (see, for example, Patent Literature 1). It is also proposed that this solid acid catalyst be used to produce ethylene and propylene as light olefins, for example, from full-range naphtha.

CITATION LIST

Patent Literature

Patent Literature 1: JP 2008-512236 W

SUMMARY OF INVENTION

Technical Problem

However, existing zeolite-based solid-acid catalysts still require high temperatures at around 650° C. for achieving high propylene yield. With respect to catalyst lifetime, there have been still no catalysts with long lifetime applicable for a fixed-bed process at commercial level.

Short catalyst lifetime is mainly due to catalyst deactivation due to coke formation.

The amount of aromatic hydrocarbons generated during cracking reactions for producing lower olefins, causing the formation of coke, is important factor, and suppressing the formation of aromatic hydrocarbons is an important key in the development of zeolite-based catalysts with long lifetime.

The production of lower olefins from naphtha using a zeolite-based solid acid catalyst can be performed by a method in which diluted feedstock is supplied to a reactor or by a method in which feedstock without dilution is employed. When the feedstock is diluted, the yields of lower olefins are more likely to increase. However, when the feedstock is diluted, the liquid hourly space velocity (LHSV) suitable for giving high yields of lower olefins may be lower than that in the undiluted case, so that a larger-size reactor may be necessary.

For example, inert gas such as nitrogen or argon, and steam can be used as the diluent. Steam can be easily separated from the products and suppress formation of aromatic hydrocarbons causing coke formation. However, steam has the serious problem of causing dealumination (aluminum atoms are often desorbed from zeolite framework under exposure to steam, so that its structure is destroyed), resulting in irrecoverable deactivation of the catalyst.

In actual propylene production, it is necessary to decide whether to dilute the feedstock or not. However, whether dilution or non-dilution is selected, the catalyst should be optimized for the selected condition.

The present invention has been accomplished in terms of the above backgrounds, and objectives of the present invention are to provide zeolite catalysts that allow reactions to proceed at temperatures as low as possible in the production of lower olefins from hydrocarbon feedstock with low boiling points such as light naphtha, make it possible to make propylene yield higher than ethylene yield in the production of lower olefins, and have long lifetime, and to provide methods for producing these zeolite catalysts and methods for producing lower olefins with these zeolite catalysts.

Solution to Problem

In order to solve the above-mentioned problems, the present invention provides zeolite catalysts for use in lower olefins production from hydrocarbon feedstock with low boiling points such as light naphtha. The zeolite catalysts are MFI-type crystalline aluminosilicates containing iron atoms and have molar ratios of iron atoms to total moles of iron atoms and aluminum atoms in the range from 0.4 to 0.7.

According these features, the zeolite catalysts for use in producing lower olefins from light naphtha or other feedstocks include MFI-type crystalline aluminosilicates containing iron atoms and have molar ratios of iron atoms to total moles of iron atoms and aluminum atoms in the range from 0.4 to 0.7. The use of these zeolite catalysts make it possible to produce propylene more preferentially than ethylene in the production of lower olefins, to suppress formation of aromatic hydrocarbons causing coke formation, and to crack hydrocarbon feedstocks with low boiling points at relatively low temperatures for the production of lower olefins.

By adding iron atoms to MFI-type crystalline aluminosilicates as solid acid catalyst, Iron plays a role to reduce the acid strength. As mentioned above, therefore, when the molar ratios of the iron atoms are in the range from 0.4 to 0.7, propylene can be produced more preferentially than ethylene in the production of lower olefins, and formation of aromatic hydrocarbons causing coke formation can be suppressed, and hydrocarbon feedstocks with low boiling points can be cracked at relatively low temperatures for the production of lower olefins.

To obtain the above advantageous effects, it is necessary to set the molar ratios of iron atoms in the range from 0.4 to 0.7. Specifically, if the molar ratios of iron atoms are less than 0.4 or more than 0.7, the production of propylene at the relatively low temperatures or the production of lower olefins including ethylene and propylene is reduced, or the formation of aromatic hydrocarbons is increased. Especially when the MFI-type crystalline aluminosilicates contain iron atoms, the acid strength can be reduced, and formation of aromatic hydrocarbons can be suppressed.

Naphtha (full range naphtha) refers to the fractions having the range of boiling points from ca. 35 to ca. 180 (200)° C. among products obtained from crude oil in atmospheric distillation process. In the naphtha, the fractions having the range of boiling points of ca. 35 to ca. 80 (100)° C. are called light naphtha, and the fractions having the range of boiling points of ca. 80 (100) to ca. 180 (200)° C. are called heavy naphtha. Light naphtha corresponds to the fractions composed mainly of pentanes having five carbon atoms and hexanes having six carbon atoms.

The hydrocarbon feedstocks with low boiling points are basically light naphtha, but the hydrocarbon feedstocks with low boiling points may contain heavy naphtha as a part of them or may be full range naphtha. Alternatively, the hydrocarbon feedstocks with low boiling points may be feedstocks other than naphtha, such as natural gas or any hydrocarbons other than petroleum, as long as they basically contain fractions corresponding to light naphtha.

In some cases, the term of "lower olefin" is defined to include olefins with less carbon atoms, such as ethylene, propylene, butene, and olefins having carbon atoms more than 4 (e.g., having 5 to 8 carbon atoms). As used herein, the term of "lower olefin" is intended to include ethylene having two carbon atoms and propylene having three carbon atoms.

"MFI" is a framework type code indicating a zeolite skeleton structure, and for example, MFI includes ZSM-5, an aluminosilicate. A database of framework type codes is made by The International Zeolite Association. Each framework type code consists of three capital alphabet letters (MFI). The framework type code indicates only the geometric structure of a zeolite skeleton, and different materials with the same geometric structure can be assigned to the same framework type code even though they have different compositions or lattice constants.

The acid density of a crystalline aluminosilicate described below is typically the molar ratio of silicon atoms to aluminum atoms, namely, the Si/Al ratio. In the present invention, the denominator further includes iron atoms or both iron atoms and gallium atoms. The lower the molar ratio of silicon atoms to total moles of aluminum atoms and iron atoms or to total moles of aluminum atoms, iron atoms, and gallium atoms in the crystalline aluminosilicate, the larger the amount of acid site. On the other hand, the higher the molar ratio, the smaller the amount of acid site.

In the present invention having the above feature, the zeolite catalysts are preferably used in the lower olefins production from the hydrocarbon feedstocks with low boiling points diluted with inert gas and/or water vapor, and the zeolite catalysts preferably have acid densities, defined as molar ratio of silicon atoms to total moles of iron atoms and aluminum atoms, in the range from 12.0 to 45.0.

According to these features, when inert gas and/or steam is used as a diluent to dilute the hydrocarbon feedstocks with low boiling points, setting the acid densities in the range from 12.0 to 45.0 makes it possible, as mentioned above, to produce propylene more preferentially than ethylene in the production of lower olefins, to suppress formation of aromatic hydrocarbons causing coke formation, and to crack the hydrocarbon feedstocks with low boiling points at relatively low temperatures for the production of lower olefins. When steam is used as a diluent, the steam can suppress deactivation of the catalyst derived from coke formation but may cause the dealumination phenomenon to degrade the catalyst as described above. Against this problem, setting the molar ratios of iron atoms as stated above and setting the acid densities in the above range make it possible to suppress the deactivation of the catalyst. For example, the inert gas may be nitrogen gas or argon gas.

In the present invention having the above features, the zeolite catalysts are preferable in the lower olefin production from the undiluted hydrocarbon feedstocks with low boiling points, and the zeolite catalysts preferably have acid densities, defined as molar ratio of silicon atoms to total moles of iron atoms and aluminum atoms, in the range from 75.0 to 200.0.

According to these features, when the hydrocarbon feedstocks with low boiling points are used without dilution, setting the acid densities in the range from 75.0 to 200.0 makes it possible, as mentioned above, to produce propylene more preferably than ethylene in the production of lower olefins, to suppress formation of aromatic hydrocarbons causing coke formation, and to crack the hydrocarbon feedstocks with low boiling points at relatively low temperatures for the production of lower olefins.

In the present invention having the above features, the MFI-type crystalline aluminosilicates preferably further contain gallium atoms in addition to iron atoms, and the zeolite catalysts preferably have molar ratios of iron atoms to total moles of iron atoms, gallium atoms, and aluminum atoms in the range from 0.2 to 0.6 and molar ratios of gallium atoms to total moles of iron atoms, gallium atoms, and aluminum atoms in the range from 0.1 to 0.4.

According to these features, the MFI-type crystalline aluminosilicates contain gallium atoms having the effect of accelerating the dehydrogenation of hydrocarbon feedstocks (alkanes) in addition to iron atoms having the effect of reducing the acid strength. In these zeolite catalysts, the molar ratios of iron atoms are in the range from 0.2 to 0.6, and the molar ratios of gallium atoms are in the range from 0.1 to 0.4, as described above. These catalysts make it possible, as mentioned above, to produce propylene more preferentially than ethylene in the production of lower olefins, to suppress formation of aromatic hydrocarbons causing coke formation, and to crack the hydrocarbon feedstocks with low boiling points at relatively low temperatures for the production of lower olefins.

In the present invention having the above features, the zeolite catalysts are preferable in the lower olefin production from the hydrocarbon feedstocks with low boiling points diluted with inert gas and/or steam, and the zeolite catalysts preferably have acid densities, defined as molar ratio of silicon atoms to total moles of iron atoms, gallium atoms, and aluminum atoms, in the range from 12.0 to 40.0.

According to these features, when the lower olefins are produced from the feedstocks with low boiling points diluted with inert gas and/or steam, setting the acid densities in the range from 12.0 to 40.0 makes it possible, as mentioned above, to produce propylene more preferentially than ethylene in the production of lower olefins, to suppress formation of aromatic hydrocarbons causing coke formation, and to crack the feedstocks with low boiling points at relatively low temperatures for the production of lower olefins. In addition, when steam is used as a diluent, the degradation of the catalyst, which seems to be caused by dealumination, can be suppressed.

In the present invention having the above features, the zeolite catalysts are preferable in the lower olefin production from the undiluted feedstocks with low boiling points, and the zeolite catalysts preferably have acid densities, defined as molar ratio of silicon atoms to moles of iron atoms, gallium atoms, and aluminum atoms, in the range from 75.0 to 200.0.

According to these features, when the lower olefins are produced from the undiluted feedstocks with low boiling points, setting the acid densities in the range from 75.0 to 200.0 makes it possible, as mentioned above, to produce propylene more preferentially than ethylene in the production of lower olefins, to suppress formation of aromatic hydrocarbons causing coke formation, and to crack the feedstocks with low boiling points at relatively low temperatures for the production of lower olefins.

In the present invention having the above features, the zeolite catalysts are preferably produced by a series of process including a hydrothermal synthesis step, a molding step, and an ion exchange step, and the hydrothermal synthesis step preferably includes synthesizing secondary particles with average sizes in the range from 0.25 µm to 1.0 µm.

According to these features, secondary particles of the crystalline aluminosilicates containing iron or both iron and gallium synthesized in the hydrothermal synthesis step have average particle sizes from 0.25 to 1.0 µm, especially, average sizes of less than 1.0 µm. For example, this makes it possible to suppress catalyst degradation caused by coke formation or the like and to extend the lifetime of the catalysts. The term of "secondary particles" is intended to include crystalline aluminosilicate particles obtained by subjecting the product of the hydrothermal synthesis reaction to steps such as separation, washing with water, drying, and calcination.

In the present invention having the above features, the zeolite catalysts are preferably produced by a process including a hydrothermal synthesis step, a molding step, and an ion exchange step, and the ion exchange step is preferably performed after the molding step.

According to these features, the ion exchange step is performed after the molding step, so that in the production of lower olefins with these zeolite catalysts, formation of aromatic hydrocarbons causing coke formation can be suppressed. In addition, the zeolite catalysts after the molding is easier to handle than the particles obtained in the hydrothermal synthesis step. In particular, it is clearly easier to handle relatively large-sized zeolite catalysts after the molding than to handle small-sized particles such as secondary particles as defined in claim 7. As a result, the operation of the ion-exchange step can be simplified.

The present invention also provides methods for producing the zeolite catalysts having the above feature. The methods includes a hydrothermal synthesis step, a molding step, and an ion exchange step, wherein the hydrothermal synthesis step includes synthesizing secondary particles with average sizes in the range from 0.25 µm to 1.0 µm.

According to these features, setting the average sizes of secondary particles in the range from 0.25 to 1.0 µm makes it possible to suppress the degradation of the catalyst and to extend the lifetime of the catalysts.

The present invention also provides methods for producing the zeolite catalysts having the above features. The methods include a hydrothermal synthesis step, a molding step, and an ion exchange step, wherein the ion exchange step is performed after the molding step.

These features make it possible, as mentioned above, to simplify the operation of the ion-exchange step and to suppress formation of aromatic hydrocarbons causing coke formation.

The present invention also provides methods for producing lower olefins from hydrocarbon feedstocks using the zeolite catalysts having the above features. The methods include performing reactions to produce the lower olefins from the hydrocarbon feedstocks with low boiling points in the presence of the zeolite catalysts in the reaction temperature range from 525° C. to 575° C.

According to these features, lower olefins are produced from the hydrocarbon feedstocks with low boiling points using the zeolite catalysts of the present invention, which makes it possible, as mentioned above, to produce propylene more preferentially than ethylene in the production of lower olefins, to suppress formation of aromatic hydrocarbons causing coke formation, and to crack the hydrocarbon feedstocks with low boiling points at relatively low temperatures for the production of lower olefins, specifically, for the production of propylene.

Advantageous Effects of Invention

The zeolite catalysts of the present invention make it possible to mainly accelerate the production of propylene at relatively low temperatures in the production of lower olefins from the hydrocarbon feedstocks with low boiling points. The present invention also makes it possible to suppress the degradation of the zeolite catalysts and to extend the lifetime of the catalysts.

BRIEF DESCRIPTION OF DRAWINGS

FIG. 1 is a graph for illustrating the experimental results in the examples according to a first embodiment of the invention.

FIG. 2 is a graph for illustrating the experimental results in the examples according to a second embodiment of the invention.

FIG. 3 is a graph for illustrating the experimental results in the examples according to a third embodiment of the invention.

DESCRIPTION OF EMBODIMENTS

Hereinafter, embodiments of the present invention are described below.

The embodiments describe zeolite catalysts for use in efficient production of lower olefins such as propylene, methods for producing such zeolite catalysts, and methods for producing lower olefins with such zeolite catalysts.

The embodiments are divided into a case where light-naphtha as feedstock for producing lower olefins is diluted with a diluent and a case where light-naphtha feedstock is not diluted, and the embodiments described for the case of dilution are also divided into a case where nitrogen gas, which is an inert gas, is used as the diluent and a case where steam is used as the diluent.

A first embodiment is described below, which provides zeolite catalysts suitable for use when light naphtha as a feedstock is diluted with nitrogen gas, methods for producing such zeolite catalysts, and methods for producing lower olefins; a second embodiment, which provides zeolite catalysts suitable for use when light naphtha as a feedstock is diluted with steam, methods for producing such zeolite catalysts, and methods for producing lower olefins; and a third embodiment, which provides zeolite catalysts suitable for use when light naphtha as a feedstock is used without dilution, methods for producing such zeolite catalysts, and methods for producing lower olefins.

Now, the first embodiment is described below.

The zeolite catalysts are iron (Fe)-containing MFI-type crystalline aluminosilicates that are produced suitable for use in the production of lower olefins under conditions using nitrogen gas (inert gas) as a diluent. The zeolite catalysts of this embodiment are preferably composite materials obtained by molding with binder.

The zeolite catalysts may include MFI-type zeolite catalysts made of crystalline aluminosilicates containing iron (Fe) for reducing acid strength and gallium (Ga) for having the effect of accelerating alkane dehydrogenation.

The iron-containing (gallium-free), MFI-type crystalline aluminosilicate zeolite catalysts preferably have molar ratios of iron atoms to total moles of iron and aluminum atoms (Fe/(Fe+Al)) of 0.4 to 0.7, more preferably 0.4 to 0.6.

The iron-containing (gallium-free), MFI-type zeolite catalysts preferably have acid densities (molar ratios of Si/(Fe+Al)) of 12.0 to 30.0, more preferably 12.0 to 25.0. The molar ratio of Si/(Fe+Al) is the molar ratio of silicon atoms to total moles of iron and aluminum atoms.

The iron and gallium-containing, MFI-type zeolite catalysts preferably have molar ratios of iron atoms to total moles of iron, gallium, and aluminum atoms (Fe/(Fe+Ga+Al)) of 0.2 to 0.6, more preferably 0.3 to 0.5.

The iron and gallium-containing, MFI-type crystalline aluminosilicate zeolite catalysts also preferably have molar ratios of gallium atoms to total moles of iron, gallium, and aluminum atoms (Ga/(Fe+Ga+Al)) of 0.1 to 0.4, more preferably 0.2 to 0.4.

The iron and gallium-containing, MFI-type zeolite catalysts also preferably have acid densities (molar ratios of Si/(Fe+Ga+Al)) of 12.0 to 40.0, more preferably 12.0 to 35.0.

The zeolite catalysts are produced by a process including a hydrothermal synthesis step, a molding step, and an ion-exchange step. In this process, the ion-exchange step is preferably performed after the molding step. The hydrothermal synthesis step preferably includes synthesizing secondary particles with average sizes from 0.25 to 1.0 μm, more preferably 0.30 to 0.9 μm.

When the zeolite catalysts of this embodiment, which are iron-containing, MFI-type crystalline aluminosilicates as described above, are used, the acid strength can be adjusted by controlling its iron contents and their acid densities, and the addition of gallium atoms makes it possible to improve the effect of accelerating alkane dehydrogenation.

According to this embodiment, when the molar ratios of iron, the molar ratios of gallium, and the acid densities are in the above ranges, respectively, the yields of propylene can be improved, for example, at reaction temperatures in the range from 525° C. to 575° C., and formation of aromatic hydrocarbons causing coke formation can be suppressed.

Zeolites for use as such solid acid catalysts (zeolite catalysts) are produced mainly through the three steps: 1. Hydrothermal synthesis step, 2. Ion-exchange step, and 3. Molding step.

1. Hydrothermal Synthesis Step

"Hydrothermal synthesis" is a generic term of method for synthesizing zeolite in the presence of water at high temperature and high pressure. Many types of zeolite of crystalline aluminosilicate are synthesized by hydrothermal synthesis. Raw materials used in the synthesis usually include a silica source (such as sodium silicate, colloidal silica, or fumed silica), an alumina source (such as aluminum hydroxide or sodium aluminate), a structure-directing agent (such as an amine), a mineralizer (such as alkali metal hydroxide), and water etc.

For the zeolite catalyst of this embodiment, an iron source (such as iron nitrate) is added to raw materials. A gallium source (such as gallium nitrate) is further preferably added. The gallium source may be supported by a binder, rather than adding the gallium source to raw materials for the MFI-type crystalline aluminosilicate as mentioned above.

These materials are mixed to prepare a highly-reactive amorphous hydrogel (mother gel), which is charged into an autoclave, a pressure reactor, and heated at ca. 150 to ca. 250° C. for a predetermined period of time to synthesize zeolite. After the hydrothermal synthesis reaction, the product is subjected to steps such as separation, washing with purified water, drying, and calcining (which is performed to decompose and remove the structure-directing agent), so that zeolite is obtained in the form of a powder.

A mother liquor gel A and another mother liquor gel B may be prepared as raw materials, in which the mother liquor gel A includes colloidal silica containing fine silica with a particle size of 8 to 11 nm as a silicon source and sodium hydroxide (NaOH) as a pH adjuster, and the mother liquor gel B contains $Al_2(SO_4)$-$nH_2O$ as an aluminum source, $Ga(NO_3)_3$-$nH_2O$ as a gallium source, $Fe(NO_3)_3$-$nH_2O$ as an iron source, and tetrapropylammonium bromide (TPrABr) as a structure-directing agent. TPrABr as a structure-directing agent is preferably added in a smaller amount.

Subsequently, the mother liquors A and B are mixed by stirring (for example, for 15 minutes). As a result, a highly-reactive amorphous hydrogel is prepared. The mother liquor gel after mixing and stirring is then aged (for example, at 60° C. overnight). For the hydrothermal synthesis, the gel is then stirred at a rotational speed of 150 rpm to 300 rpm at 120° C. to 150° C. Thus, crystallization is performed at a high temperature and a high pressure. However, the reaction temperature is relatively low, and nuclei are grown at a low temperature so that the production of coarse particles is suppressed. The stirring speed is relatively high so that the nuclei are produced in a large amount. Under such conditions, the stirring is performed, for example, for 24 hours, so that crystals are obtained. The resultant crystals are washed with purified water and dewatered by centrifugation. Subsequently, the crystals are, for example, dried at 120° C. for 3 hours and then calcined at 550° C. for 3 hours so that TPrABr is removed. When the gallium-free material is produced, no gallium source is added to the mother liquor gel B.

2. Ion-Exchange Step

Many chemical reactions with the aid of zeolite as a catalyst are performed using the properties of a solid acid, in which the properties of the acid are produced by introducing acidic OH groups (Broensted acid sites) into zeolite.

To produce the acid properties, an ion-exchange reaction is generally used. Usually, zeolite obtained by hydrothermal synthesis contains sodium cations (Na$^+$) to keep charge balance. Such sodium cations are replaced with protons (H$^+$) by ion-exchange. Alternatively, sodium cations may be exchanged for protons (H$^+$) by a process including temporarily replacing sodium cations with ammonium ions (NH$_4^+$) by ion-exchange using a NH$_4$NO$_3$ solution and then drying and calcining the product to remove ammonia.

3. Molding Step

In general, when used industrially as a catalyst, zeolite is often molded into a cylindrical shape or any other shape in view of improvement of mechanical properties or reduction of pressure loss. This step may include kneading the zeolite material with a binder such as an alumina powder, molding, drying and calcining the mixture, etc. For example, the molding is performed using extrusion molding or the like.

For example, alumina (aluminum oxide) is added as a binder to powdery zeolite obtained through the hydrothermal synthesis step (or the ion-exchange step), and the mixture is kneaded, molded (for example, into a 1.0 mm$\phi$ thin circular cylinder or cylindrical tube), and then dried, for example, at 120° C. for 3 hours. Subsequently, the dried product is calcined at 550° C. for 3 hours, so that a zeolite catalyst made of a composite of aluminum oxide and iron (and gallium)-containing MFI-type zeolite as described above is obtained. Although the molding step may be performed before or after the ion-exchange step, the ion-exchange step is preferably performed after the molding step.

When the ion-exchange step is performed after the molding step, formation of aromatic hydrocarbons causing coke formation is successfully suppressed in the process of producing lower olefins with the zeolite catalyst. In addition, the molded zeolite catalyst obtained after the molding step is easier to handle than the powdery crystalline aluminosilicate obtained after the hydrothermal synthesis step and thus can improve the operability of the ion-exchange step.

Such zeolite catalysts can be used in a method for producing low olefins from light naphtha. In this method, for example, a hydrocarbon feedstock diluted with nitrogen as a diluent is supplied to a reactor. Thus, the hydrocarbon feedstock is brought into contact with the catalyst in the presence of nitrogen when allowed to react. A method that may be used includes placing the zeolite catalyst as a fixed bed in the reactor, supplying a feedstock into the reactor, and allowing the feedstock to pass through the reactor while bringing the feedstock into contact with the zeolite catalyst. In this process, the reaction is allowed to proceed in a moderate temperature range from 525° C. to 575° C., preferably 540° C. to 575° C., to produce ethylene and propylene.

When the zeolite catalysts, the zeolite-catalyst-producing methods, and the lower-olefin-producing methods described above are used, propylene can be successfully produced efficiently by catalytic naphtha-cracking process in low temperature range from ca. 525° C. to ca. 575° C. In addition, the reaction proceeds at relatively low temperatures, which are advantageous in that renewable energy such as solar heat or various types of unutilized waste heat can be used as the heat source. The zeolite catalysts of this embodiment work stably even in the presence of nitrogen and reduce significantly the selectivity to aromatic compounds (or suppresses aromatic compound production), so that catalyst deactivation associated with coke formation can be remarkably suppressed.

Next, the second embodiment is described below.

The zeolite catalysts of this embodiment are iron (Fe)-containing, MFI-type crystalline aluminosilicates with lower acid densities, which are produced suitable for use in the production of lower olefins under conditions using steam as a diluent. The zeolite catalysts are preferably composite materials obtained by molding with binder. In these cases, gallium may be supported by the binder, and the composite materials may contain gallium.

The zeolite catalysts may include MFI-type zeolite catalysts made of crystalline aluminosilicates containing iron (Fe) for reducing acid strength and gallium (Ga) having the effect of accelerating alkane dehydrogenation.

The iron-containing (gallium-free), MFI-type crystalline aluminosilicate zeolite catalysts preferably have molar ratios of iron atoms to total moles of iron atoms and aluminum atoms (Fe/(Fe+Al)) of 0.5 to 0.6.

The iron-containing (gallium-free), MFI-type zeolite catalysts preferably have acid densities (molar ratios of Si/(Fe+Al)) of 25.0 to 45.0. The molar ratio of Si/(Fe+Al) is the molar ratio of silicon atoms to total moles of iron and aluminum atoms.

The iron and gallium-containing, MFI-type zeolite catalysts preferably have molar ratios of iron atoms to total moles of iron, gallium, and aluminum atoms (Fe/(Fe+Ga+Al)) of 0.2 to 0.6, more preferably 0.3 to 0.5.

The iron and gallium-containing, MFI-type crystalline aluminosilicate zeolite catalysts also preferably have molar ratios of gallium atoms to total moles of iron, gallium, and aluminum atoms (Ga/(Fe+Ga+Al)) of 0.1 to 0.4, more preferably 0.2 to 0.4.

The iron and gallium-containing, MFI-type zeolite catalysts also preferably have acid densities (molar ratios of Si/(Fe+Ga+Al)) of 25.0 to 40.0, more preferably 25.0 to 35.0. The molar ratio of Si/(Fe+Ga+Al) is the molar ratio of silicon atoms to total moles of iron, gallium, and aluminum atoms.

When the zeolite catalysts of this embodiment, which are iron-containing, MFI-type crystalline aluminosilicates as described above, are used, the acid strength can be adjusted by controlling its iron contents and their acid densities, and the addition of gallium makes it possible to improve the effect of accelerating alkane dehydrogenation.

According to this embodiment, when the molar ratios of iron atoms, the molar ratios of gallium atoms, and the acid densities are in the above ranges, respectively, the yields of propylene can be improved, for example, at reaction temperatures in the range from 525° C. to 575° C., and catalyst deactivation, which is attributed to dealumination caused in the presence of steam, can be suppressed.

When gallium supported on a binder is subjected to calcining as described above, it is preferred that the molar ratio of gallium should be substantially the same as that in the gallium-containing zeolite catalyst described above. In this case, alumina as a binder is not counted in the number of moles of aluminum.

Zeolites for use as such solid acid catalyst (zeolite catalyst) are produced through the three steps: 1. Hydrothermal synthesis step, 2. Ion-exchange step, and 3. Molding step in substantially the same manner as in the first embodiment.

For the zeolite catalysts of this embodiment, an iron source (e.g., iron nitrate) is added to raw materials. In addition, a gallium source (e.g., gallium nitrate) is preferably added. The gallium source may be supported by a binder as mentioned above, rather than adding it to raw materials for the MFI-type crystalline aluminosilicate.

Such zeolite catalysts may be used in a method for producing low olefins from light naphtha. In this method, for example, a hydrocarbon feedstock diluted with steam as a diluent is supplied to a reactor. Thus, the hydrocarbon feedstock is brought into contact with the catalyst in the presence of steam when allowed to react. A method that may be used includes placing the zeolite catalyst as a fixed bed in the reactor, supplying a feedstock into the reactor, and allowing the feedstock to pass through the reactor while bringing the feedstock into contact with the zeolite catalyst. In this process, the reaction is allowed to proceed in a moderate temperature range from 525° C. to 575° C., preferably 540° C. to 575° C., to produce ethylene and propylene.

When the zeolite catalysts, the zeolite-catalyst-producing methods, and the lower-olefin-producing methods described above are used, propylene can be successfully produced efficiently by catalytic naphtha-cracking process in a low temperature range of ca. 525 to ca. 575° C. In addition, the reaction proceeds at relatively low temperatures, which are advantageous in that renewable energy such as solar heat or various types of unutilized waste heat can be used as the heat source. The zeolite catalysts of this embodiment work stably even in the presence of steam and reduce significantly the selectivity to aromatic compounds (or suppresses aromatic compound production), so that catalyst deactivation associated with coke formation can be remarkably suppressed.

Next, the third embodiment is described below.

The zeolite catalysts of this embodiment are iron (Fe)-containing, MFI-type crystalline aluminosilicates with lower acid densities, which are produced suitable for use in the production of lower olefins under undiluted conditions without any diluent (such as steam and/or inert gas). The zeolite catalysts of this embodiment are preferably composite materials obtained by molding with binder.

The zeolite catalysts may include MFI-type zeolite catalysts made of crystalline aluminosilicates containing iron (Fe) for reducing acid strength and gallium (Ga) having the effect of accelerating alkane dehydrogenation.

The iron-containing (gallium-free), MFI-type crystalline aluminosilicate zeolite catalysts preferably have molar ratios of iron atoms to total moles of iron and aluminum atoms (Fe/(Fe+Al)) of 0.4 to 0.7, more preferably 0.4 to 0.6.

The iron-containing (gallium-free), MFI-type zeolite catalysts preferably have acid densities (molar ratios of Si/(Fe+Al)) of 75.0 to 200.0, more preferably 80.0 to 200.0. The molar ratio of Si/(Fe+Al) is the molar ratio of silicon atoms to total moles of iron and aluminum atoms.

The iron and gallium-containing, MFI-type zeolite catalysts preferably have molar ratios of iron atoms to total moles of iron, gallium, and aluminum atoms (Fe/(Fe+Ga+Al)) of 0.2 to 0.6, more preferably 0.3 to 0.5.

The iron and gallium-containing, MFI-type crystalline aluminosilicate zeolite catalysts also preferably have molar ratios of gallium atoms to total moles of iron, gallium, and aluminum atoms (Ga/(Fe+Ga+Al)) of 0.1 to 0.4, more preferably 0.2 to 0.4.

The iron and gallium-containing, MFI-type zeolite catalysts also preferably have acid densities (molar ratios of Si/(Fe+Ga+Al)) of 75.0 to 200.0, more preferably 80.0 to 200.0. The molar ratio of Si/(Fe+Ga+Al) is the molar ratio of silicon atoms to total moles of iron, gallium, and aluminum atoms.

When the zeolite catalysts of this embodiment, which are iron-containing, MFI-type crystalline aluminosilicates as described above, are used, the acid strength can be adjusted by controlling its iron contents and its acid densities, and the addition of gallium makes it possible to improve the effect of accelerating alkane dehydrogenation.

According to this embodiment, when the molar ratio of iron, the molar ratio of gallium, and the acid densities are in the above ranges, respectively, the yields of propylene can be improved, for example, at a reaction temperature in the range from 525° C. to 575° C., and formation of aromatic carbon causing coke formation can be suppressed.

Especially when the Si/(Fe+Al) ratios and Si/(Fe+Ga+Al) ratios are of above 75.0 as mentioned above, propylene production can be accelerated, and formation of aromatic hydrocarbons can be suppressed, and when Si/(Fe+Al) ratios and Si/(Fe+Ga+Al) ratios are of below 200.0 as mentioned above, propylene production can be prevented from being suppressed.

Zeolites for use as such solid acid catalyst (zeolite catalysts) are produced through the three steps: 1. Hydrothermal synthesis step, 2. Ion-exchange step, and 3. Molding step in substantially the same manner as in the first embodiment.

Such zeolite catalysts may be used in a method for producing low olefins from light naphtha. In this method, for example, a hydrocarbon feedstock is supplied without dilution to a reactor. A method that may be used includes placing the zeolite catalyst as a fixed bed in the reactor, supplying a feedstock into the reactor, and allowing the feedstock to pass through the reactor while bringing the feedstock into contact with the zeolite catalyst. In this process, the reaction is allowed to proceed in a moderate temperature range from 525° C. to 575° C., preferably 540° C. to 575° C., to produce ethylene and propylene.

When the zeolite catalysts, the zeolite-catalyst-producing methods, and the lower-olefin-producing methods described above are used, propylene can be successfully produced efficiently by catalytic naphtha-cracking process in a low temperature range from ca. 525° C. to ca. 575° C. In addition, the reaction proceeds at relatively low temperatures, which are advantageous in that renewable energy such as solar heat or various types of unutilized waste heat can be used as the heat source. Since the LHSV in the region where the reaction proceeds is higher when feedstock without dilution is supplied than when a hydrocarbon feedstock is supplied in the presence of a diluent, the space time yield can be increased in the case of supplying feedstock without dilution, and the reactor can be designed to be compact. In other words, there is no increase in volume of feedstock due to dilution, and the reaction equipment can be made compact.

When a feedstock such as light naphtha is diluted as in the first and second embodiments, a mixture of different types of inert gas may be used, or a mixture of inert gas and steam may be used.

Therefore, although the embodiments are divided into a case where a feedstock such as light naphtha is diluted with inert gas and a case where a raw material is diluted with steam, they may be divided into an undiluted case where a feedstock is not diluted and a case where a feedstock is diluted.

When a feedstock is diluted with inert gas and/or steam vapor, the iron-containing, gallium-free, zeolite catalysts preferably have acid densities in the range from 12.0 to 45.0, wherein the acid density is defined as the molar ratio of silicon atoms to moles of iron and aluminum atoms.

EXAMPLES

Next, a first example of the present invention is described below.

The first example corresponds to the first embodiment described above, according to which zeolite catalysts of Examples 1 to 6 shown in Tables 1 to 7 below were experimentally produced, while zeolite catalysts of Comparative Examples 1 to 4 were experimentally produced, and lower olefins were produced using the produced zeolite catalysts of Examples 1 to 6 and Comparative Examples 1 to 4, respectively.

The zeolite catalyst of Example 1 is a zeolite catalyst containing both iron atoms and gallium atoms according to the above embodiment, and the zeolite catalyst of Example 2 is a zeolite catalyst containing iron atoms but not containing gallium atoms according to the above embodiment.

The zeolite catalyst of Comparative Example 1 is a zeolite catalyst containing neither iron atoms nor gallium atoms, for example, ZSM-5, and the zeolite catalyst of Comparative Example 2 is a zeolite catalyst containing gallium atoms but not containing iron atoms. The zeolite catalysts of Examples 1 and 2 and Comparative Examples 1 and 2 do not undergo the steps of addition of binder and consequent calcination but undergo ion-exchange steps without any molding step.

The zeolite catalyst of Example 3 undergoes the step of addition of binder and consequent calcination and undergoes an ion-exchange step before a molding step. The zeolite catalyst of Example 4 undergoes the step of addition of binder and consequent calcination and undergoes an ion-exchange step after a molding step.

The zeolite catalysts of Examples 5 and 6 are modified from the zeolite catalyst containing iron, gallium, and aluminum atoms of Example 4 by varying the acid density. The zeolite catalyst of Comparative Example 3 is an analog of the zeolite catalyst of Example 4 but has an acid density of above 40.0. The zeolite catalyst of Comparative Example 4 is an analog of the zeolite catalyst of Example 6 but undergoes a hydrothermal synthesis step in which the average size of secondary particles of crystalline aluminosilicate is larger than the above-mentioned 1.0 μm.

Hereinafter, Examples 1 to 6 and Comparative Examples 1 to 4 are described.

TABLE 1

Listing of compositions and particle sizes of different MFI-type zeolites

|  | Comparative Example 1 | Comparative Example 2 | Example 1 | Example 2 |
|---|---|---|---|---|
| Zeolite species | H-Al-MFI | H-GaAl-MFI | H-FeGaAl-MFI | H-FeAl-MFI |
| Acid density (Si/(Fe + Ga + Al)) [mol/mol] | 20.0 | 20.3 | 19.4 | 19.4 |
| Molar ratio of Fe (Fe/(Fe + Ga + Al)) | 0.0 | 0.0 | 0.4 | 0.5 |
| Molar ratio of Ga (Ga/(Fe + Ga + Al)) | 0.0 | 0.3 | 0.3 | 0.0 |
| Molar ratio of Al (Al/(Fe + Ga + Al)) | 1.0 | 0.7 | 0.3 | 0.5 |
| Average particle size (secondary particle size) [μm] | 0.90 | 0.94 | 0.38 | 0.46 |

TABLE 2

Comparison of catalytic performance of different MFI-type zeolites

|  | Comparative Example 1 | Comparative Example 2 | Example 1 | Example 2 |
|---|---|---|---|---|
| Zeolite species | H-Al-MFI | H-GaAl-MFI | H-FeGaAl-MFI | H-FeAl-MFI |
| Reaction temperature [° C.] | 550 | 550 | 550 | 550 |
| Charged amount of catalyst [mL] | 1.0 | 1.0 | 1.0 | 1.0 |
| LHSV (based on n-hexane) [h$^{-1}$] | 1.0 | 1.0 | 1.0 | 1.0 |
| Total pressure [MPa] | 0.1 | 0.1 | 0.1 | 0.1 |
| Mixed ratio of $N_2$/n-hexane [mol/mol] | 15/1 | 15/1 | 15/1 | 15/1 |
| n-hexane conversion [wt %] | 99.9 | 99.7 | 71.8 | 74.9 |
| Ethylene yield [wt %] | 23.4 | 15.8 | 8.3 | 8.7 |
| Propylene yield [wt %] | 16.3 | 6.9 | 27.0 | 24.7 |
| Yield of aromatic hydrocarbons [wt %] | 14.2 | 49.4 | 7.1 | 7.3 |

TABLE 3

Comparison of the characteristics of FeGaAl-MFI catalyst and FeGaAl-MFI/Al$_2$O$_3$ composite catalyst

|  | Example 1 | Example 3 | Example 4 |
|---|---|---|---|
| Zeolite species | FeGaAl-MFI | FeGaAl-MFI | FeGaAl-MFI |
| Acid density (Si/(Fe + Ga + Al)) | 19.4 | 19.4 | 19.4 |
| Molar ratio of Fe (Fe(Fe + Ga + Al)) | 0.4 | 0.4 | 0.4 |
| Molar ratio of Ga (Ga/(Fe + Ga + Al)) | 0.3 | 0.3 | 0.3 |
| Molar ratio of Al (Al/(Fe + Ga + Al)) | 0.3 | 0.3 | 0.3 |
| Binder type used for molding | Absent (zeolite powder is pelletized) | Al$_2$O$_3$ powder (AP-1) | Al$_2$O$_3$ powder (AP-1) |
| Methods for molding and ion exchange | Na-type zeolite is converted to H-type and then pelletized | Na-type zeolite is converted to H-type and then extrusion-molded | Na-type zeolite and alumina are extrusion-molded and then converted to H-type |
| Mixed ratio of zeolite/binder [wt %/wt %] | 100/0 | 65/35 | 65/35 |

TABLE 4

Comparison of the performance of FeGaAl-MFI catalyst and FeGaAl-MFI/Al$_2$O$_3$ composite catalyst

|  | Example 1 | Example 3 | Example 4 |
|---|---|---|---|
| Zeolite species | FeGaAl-MFI | FeGaAl-MFI | FeGaAl-MFI |
| Acid density (Si/(Fe + Ga + Al)) [mol/mol] | 19.4 | 19.4 | 19.4 |
| Mixed ratio of zeolite/binder [wt %/wt %] | 100/0 | 65/35 | 65/35 |
| Reaction temperature [° C.] | 550 | 550 | 550 |
| Charged amount of catalyst [mL] | 1.0 | 1.0 | 1.0 |
| LHSV (based on n-hexane) [h$^{-1}$] | 1.0 | 1.0 | 1.0 |
| Total pressure [MPa] | 0.1 | 0.1 | 0.1 |
| Mixed ratio of N$_2$/n-hexane [mol/mol] | 15/1 | 15/1 | 15/1 |
| n-hexane conversion [wt %] | 71.8 | 81.5 | 80.9 |
| Ethylene yield [wt %] | 8.3 | 8.9 | 10.0 |
| Propylene yield [wt %] | 27.0 | 29.1 | 28.3 |
| Yield of aromatic hydrocarbons [wt %] | 7.1 | 17.5 | 10.8 |
| Propylene space time yield [g-C$_3$H$_6$/g-zeolite · h] | 0.40 | 0.54 | 0.53 |

TABLE 5

Listing of compositions of FeGaAl-MFI/Al$_2$O$_3$ composite catalysts with different acid densities

|  | Comparative Example 3 | Example 5 | Example 4 | Example 6 |
|---|---|---|---|---|
| Zeolite species | FeGaAl-MFI | FeGaAl-MFI | FeGaAl-MFI | FeGaAl-MFI |
| Acid density (Si/(Fe + Ga + Al)) | 50.1 | 31.3 | 19.4 | 12.0 |
| Molar ratio of Fe (Fe/(Fe + Ga + Al)) | 0.4 | 0.4 | 0.4 | 0.4 |
| Molar ratio of Ga (Ga/(Fe + Ga + Al)) | 0.3 | 0.3 | 0.3 | 0.3 |
| Molar ratio of Al (Al/(Fe + Ga + Al)) | 0.3 | 0.3 | 0.3 | 0.3 |
| Average particle size (secondary particle size) [μm] | 0.90 | 0.81 | 0.38 | 0.57 |
| Binder type used for molding | Al$_2$O$_3$ powder (AP-1) | Al$_2$O$_3$ powder (AP-1) | Al$_2$O$_3$ powder (AP-1) | Al$_2$O$_3$ powder (AP-1) |
| Mixed ratio of zeolite/binder [wt %/wt %] | 65/35 | 65/35 | 65/35 | 65/35 |

TABLE 6

Comparison of the performance of FeGaAl-MFI/Al$_2$O$_3$ composite catalysts with different acid densities

|  | Comparative Example 3 | Example 5 | Example 4 | Example 6 |
|---|---|---|---|---|
| Zeolite species | FeGaAl-MFI | FeGaAl-MFI | FeGaAl-MFI | FeGaAl-MFI |
| Acid density (Si/(Fe + Ga + Al)) | 50.1 | 31.3 | 19.4 | 12.0 |
| Mixed ratio of zeolite/binder [wt %/wt %] | 65/35 | 65/35 | 65/35 | 65/35 |
| Reaction temperature [° C.] | 550 | 550 | 550 | 550 |
| Charged amount of catalyst [mL] | 1.0 | 1.0 | 1.0 | 1.0 |

TABLE 6-continued

Comparison of the performance of FeGaAl-MFI/Al$_2$O$_3$ composite catalysts with different acid densities

| | Comparative Example 3 | Example 5 | Example 4 | Example 6 |
|---|---|---|---|---|
| LHSV (based on n-hexane) [h$^{-1}$] | 1.0 | 1.0 | 1.0 | 1.0 |
| Total pressure [MPa] | 0.1 | 0.1 | 0.1 | 0.1 |
| Mixed ratio of N$_2$/n-hexane [mol/mol] | 15/1 | 15/1 | 15/1 | 15/1 |
| n-hexane conversion [wt %] | 36.8 | 46.1 | 80.9 | 85.6 |
| Ethylene yield [wt %] | 2.8 | 3.7 | 10.0 | 9.8 |
| Propylene yield [wt %] | 15.2 | 20.0 | 28.3 | 31.2 |
| Yield of aromatic hydrocarbons [wt %] | 1.4 | 2.1 | 10.8 | 15.9 |

TABLE 7

Listing of conditions of synthesis and compositions of FeGaAl-MFI zeolites with different particle sizes

| | Comparative Example 4 | Example 6 |
|---|---|---|
| Zeolite species | FeGaAl-MFI | FeGaAl-MFI |
| Structure-directing agent/(Fe + Ga + Al) ratio [mol/mol] | 5.70 | 2.85 |
| Aging of mother gel (raw material for zeolite) | Absent | Present (60° C., overnight) |
| Synthesis temperature [° C.]/stirring speed [rpm] | 180/150 | 150/300 |
| Average particle size (secondary particle size) of zeolite species [μm] | 6.30 | 0.57 |
| Acid density (Si/(Fe + Ga + Al)) | 11.8 | 12.0 |
| Molar ratio of Fe (Fe/(Fe + Ga + Al)) | 0.4 | 0.4 |
| Molar ratio of Ga (Ga/(Fe + Ga + Al)) | 0.3 | 0.3 |
| Molar ratio of Al (Al/(Fe + Ga + Al)) | 0.3 | 0.3 |
| Binder type used for molding | Al$_2$O$_3$ powder (AP-1) | Al$_2$O$_3$ powder (AP-1) |
| Mixed ratio of zeolite/binder [wt %/wt %] | 65/35 | 65/35 |

Example 1

It is described below how to synthesize FeGaAl-MFI zeolite in Example 1.

Liquids A and B were prepared, in which the liquid A was a solution composed of 58.9 g of colloidal silica (30.6 wt % of SiO$_2$, 0.4 wt % of Na$_2$O, and 69.0 wt % of H$_2$O) and 2.99 g of sodium hydroxide, and the liquid B was a solution composed of 1.52 g of aluminum sulfate n-hydrate, 0.88 g of gallium nitrate n-hydrate, 1.96 g of iron nitrate 9-hydrate, 9.29 g of tetrapropylammonium bromide, and 186.3 g of water. The liquids A and B were gradually mixed by stirring at room temperature, and the mixture was then further vigorously stirred for 15 minutes in a mixer.

The mixture solution was allowed to stand overnight while its temperature was kept at 60° C. Subsequently, the mixture solution was subjected to a hydrothermal synthesis reaction at its own pressure in an autoclave under the conditions of 150° C., 24 hours, and 300 rpm. After cooled, the product was thoroughly washed with purified water (the solid and the aqueous solution were separated using a centrifuge). Subsequently, the product was dried at 120° C. for 3 hours and then calcined at 550° C. for 3 hours in an air stream, so that Fe, Ga, and Al-containing, Na-type MFI zeolite (hereinafter abbreviated as FeGaAl-MFI zeolite) was synthesized. The molar ratio of each element in the zeolite and the average particle size of secondary particles of the zeolite were measured by fluorescent X-ray analysis and laser scattering/diffraction analysis, respectively.

The above-mentioned Na-type FeGaAl-MFI zeolite was subjected to ion-exchange using a 2.2 mol/L ammonium nitrate aqueous solution under boiling and refluxing conditions, and then washed with purified water. This process was repeated four times (in which each ion exchange was performed for 2 hours, and the 2.2 mol/L ammonium nitrate aqueous solution was replaced with new one every time). Subsequently, the product was dried at 120° C. for 3 hours and then calcined at 550° C. for 3 hours in an air stream to give proton-type FeGaAl-MFI zeolite.

The resultant FeGaAl-MFI zeolite had the following molar ratios of elements: Si/(Fe+Ga+Al)=19.4 (acid density), Fe/(Fe+Ga+Al)=0.4, Ga/(Fe+Ga+Al)=0.3, and Al/(Fe+Ga+Al)=0.3, and an average particle size of 0.38 μm (see Table 1).

Next, it is described below how to evaluate the performance of the FeGaAl-MFI zeolite catalyst.

The powdery proton-type FeGaAl-MFI zeolite synthesized according to the above procedure was formed into a tablet, and then ground and sized to give a catalyst sample for use in performance evaluation. Catalytic cracking of n-hexane was carried out in a fixed-bed-type reactor in order to evaluate catalytic performance of this zeolite.

The catalyst of 1.0 mL was charged into a stainless-steel tubular reactor (made of SUS 316) with an inner diameter of 8.0 mm in such a manner that a catalyst layer with height of ca. 20 mm was formed. Glass wool was packed before and after the catalyst layer, and glass beads were charged before and after the glass wool.

The catalytic cracking reaction of n-hexane was performed for 5 hours under the reaction conditions of: a reaction temperature of 550° C. (the temperature was raised over 1 hour in a nitrogen stream until the temperature of the catalyst layer reached 550° C.); a total pressure of 0.1 MPa; a n-hexane flow rate of 0.65 g/h (liquid hourly space velocity (LHSV) based on n-hexane: 1.0 h$^{-1}$); and a nitrogen flow rate of 2.55 NL/h (N$_2$/n-hexane=15 mol/mol).

The reaction products were examined by gas-chromatographic analysis every one hour, in which the feedstock (n-hexane) conversion (wt %), the yield (wt %) of lower olefins (ethylene and propylene), and the yield (wt %) of aromatic hydrocarbons were determined as factors exhibiting catalytic performance. Table 2 shows the results of the present sample after 5 hours from the start of the reaction.

Example 2

It is described below how to synthesize FeAl-MFI zeolite in Example 2.

Proton-type FeAl-MFI zeolite was synthesized in the same manner as in Example 1, except that a solution composed of 2.28 g of aluminum sulfate n-hydrate, 1.96 g of iron nitrate 9-hydrate, 9.29 g of tetrapropylammonium bromide, and 186.2 g of water was used instead as the liquid B. The resultant FeAl-MFI zeolite had the following molar ratios of elements: Si/(Fe+Al)=19.4 (acid density), Fe/(Fe+Al)=0.5, and Al/(Fe+Al)=0.5, and an average particle size of 0.46 μm (see Table 1).

Next, it is described below how to evaluate the performance of the FeAl-MFI zeolite catalyst.

The catalytic performance of the FeAl-MFI zeolite was evaluated in the same way as in Example 1. Table 2 shows the results of the present sample after 5 hours from the start of the reaction.

Comparative Example 1

It is described below how to synthesize Al-MFI zeolite in Comparative Example 1.

Proton-type Al-MFI zeolite was synthesized in the same manner as in Example 1, except that a solution composed of 3.80 g of aluminum sulfate n-hydrate, 9.29 g of tetrapropylammonium bromide, and 186.4 g of water was used instead as the liquid B. The resultant Al-MFI zeolite had a molar ratio of aluminum (Si/Al) of 20.0 and an average particle size of 0.90 μm (see Table 1).

Next, it is described below how to evaluate the performance of the Al-MFI zeolite catalyst.

The catalytic performance of the Al-MFI zeolite was evaluated in the same way as in Example 1. Table 2 shows the results of the present sample after 5 hours from the start of the reaction.

Comparative Example 2

It is described below how to synthesize a GaAl-MFI zeolite in Comparative Example 2.

Proton-type GaAl-MFI zeolite was synthesized in the same manner as in Example 1, except that a solution composed of 3.04 g of aluminum sulfate n-hydrate, 0.88 g of gallium nitrate n-hydrate, 9.29 g of tetrapropylammonium bromide, and 186.3 g of water was used instead as the liquid B. The resultant GaAl-MFI zeolite had the following molar ratios of elements: Si/(Ga+Al)=20.3 (acid density), Ga/(Ga+Al)=0.3, and Al/(Ga+Al)=0.7, and an average particle size of 0.94 μm (see Table 1).

Next, it is described below how to evaluate the performance of the GaAl-MFI zeolite catalyst.

The catalytic performance of the GaAl-MFI zeolite was evaluated in the same way as in Example 1. Table 2 shows the results of the present sample after 5 hours from the start of the reaction.

Table 2 shows that as compared with a conventional type, ZSM-5 (Al-MFI zeolite of Comparative Example 1), the FeGaAl-MFI zeolite containing both iron having the effect of reducing acid strength and gallium having the effect of accelerating alkane dehydrogenation significantly improved the propylene yield and suppressed formation of aromatic hydrocarbons (Example 1). It was also found that the FeAl-MFI zeolite containing iron also significantly improved the propylene yield and suppressed formation of aromatic hydrocarbons (Example 2).

On the other hand, when the GaAl-MFI zeolite containing gallium (Comparative Example 2) was used, aromatic hydrocarbons were dominantly formed, resulting in the lowest yield of propylene. When the catalyst samples of Examples 1 and 2 and Comparative Examples 1 and 2 were used, no reduction in conversion (catalyst degradation caused by coke formation or the like) was observed within 5 hours.

Example 3

It is described below how to prepare a FeGaAl-MFI zeolite (Si/(Fe+Ga+Al)=19.4)/alumina composite catalyst in Example 3.

The powdery proton-type FeGaAl-MFI zeolite (4.0 wt % in water content) of Example 1 and alumina powder (Cataloid AP-1, 71.7 wt % in $Al_2O_3$ content, JGC Catalysts and Chemicals Ltd.) were kneaded while a proper amount of purified water was added to them, so that a massive zeolite/alumina mixture was obtained. The mixture was then formed into a cylindrical composite (1.0 mmφ) using an extruder. The composite was dried at 120° C. for 3 hours and then calcined at 550° C. for 3 hours in an air stream, so that a FeGaAl-MFI zeolite/alumina composite catalyst was obtained.

Using fluorescent X-ray analysis, the weight composition of the catalyst was determined to be zeolite/alumina ratio of 65 wt %/35 wt % (see Table 3).

Next, it is described below how to evaluate the performance of the FeGaAl-MFI zeolite (Si/(Fe+Ga+Al)=19.4)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. Table 4 shows the results of the present sample after 5 hours from the start of the reaction.

Example 4

It is described below how to prepare a FeGaAl-MFI zeolite (Si/(Fe+Ga+Al)=19.4)/alumina composite in Example 4.

The powdery Na-type FeGaAl-MFI zeolite of Example 1 and alumina powder were used and molded in the same way as in Example 3, so that a cylindrical FeGaAl-MFI zeolite/alumina composite was obtained. The composite was then subjected to ion-exchange to prepare a FeGaAl-MFI zeolite/alumina composite catalyst. The ion-exchange was performed in the same way as in Example 1.

Using fluorescent X-ray analysis, the weight composition of the catalyst was determined to be zeolite/alumina ratio of 65 wt %/35 wt % (see Table 3).

Next, it is described below how to evaluate the performance of the FeGaAl-MFI zeolite (Si/(Fe+Ga+Al)=19.4)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. Table 4 shows the results of the present sample after 5 hours from the start of the reaction.

In general, zeolite-based catalysts for industrial use are often mixed with a binder and molded into certain shapes so that mechanical properties can be improved or pressure loss can be reduced. In the present invention, therefore, extrusion-molded catalyst samples were prepared using an alumina binder as the example of molded zeolite and examined for their performance. Table 4 shows the performance of the composite catalysts consisting of the FeGaAl-MFI zeolite and alumina (Examples 3 and 4) in comparison with the catalytic performance of the FeGaAl-MFI zeolite alone (Example 1).

When the composite catalysts were used, the conversion of feedstock, the propylene yield, and the space time yield* of propylene were higher than those in the case of zeolite alone.

*In the present invention, the space time yield of propylene (g-$C_3H_6$/g-zeolite·h) was defined as the weight of propylene that can be produced per hour by zeolite of one gram. In the reaction test according to the present invention, the charged volume of the catalysts was uniformly 1.0 mL. As a consequence, the weight of the zeolite in the composite catalysts in Examples 3 and 4 were smaller than that in Example 1.

The sample prepared by molding the powdery Na-type zeolite and then converting the molded one to proton-type one (Example 4) gave lower the yield of aromatic hydrocarbons than that of the sample prepared by converting the powdery Na-type zeolite to proton-type one and then molding proton-type one (Example 3). In addition to this experimental result, the procedure (Example 4) of molding the powdery Na-type zeolite before the ion-exchange step is easier to handle than that (Example 3) of performing the ion-exchange step prior to the molding step. It has been thus found that the preparation method of performing extrusion-molding firstly and performing ion-exchange secondary (Example 4) is more preferred.

From these results, it has been found that the FeGaAl-MFI zeolite has high catalytic performance even when it forms a molded composite with an alumina binder. When the catalyst samples of Examples 3 and 4 were used, no reduction in conversion (catalyst degradation caused by coke formation or the like) was observed within 5 hours.

Example 5

Next, it is described below how to prepare a FeGaAl-MFI zeolite (Si/(Fe+Ga+Al)=31.3)/alumina composite.

Na-type FeAl-MFI zeolite was synthesized in the same manner as in Example 1, except that a solution composed of 58.9 g of colloidal silica (30.6 wt % of $SiO_2$, 0.4 wt % of $Na_2O$, and 69.0 wt % of $H_2O$) and 2.25 g of sodium hydroxide was used instead as the liquid A and that a solution composed of 0.76 g of aluminum sulfate n-hydrate, 0.44 g of gallium nitrate n-hydrate, 0.98 g of iron nitrate 9-hydrate, 4.65 g of tetrapropylammonium bromide, and 187.2 g of water was used instead as the liquid B.

In addition, the resultant powdery Na-type FeGaAl-MFI zeolite and alumina powder were used and molded in the same way as in Example 4, so that a cylindrical FeGaAl-MFI zeolite/alumina composite was obtained.

The composite was then subjected to ion-exchange to prepare a FeGaAl-MFI zeolite/alumina composite catalyst. The ion-exchange was performed in the same way as in Example 1. The resultant FeGaAl-MFI zeolite had the following molar ratios of elements: Si/(Fe+Ga+Al)=31.3 (acid density), Fe/(Fe+Ga+Al)=0.4, Ga/(Fe+Ga+Al)=0.3, and Al/(Fe+Ga+Al)=0.3, and an average particle size of 0.81 μm, and the weight composition of the composite catalyst was zeolite/alumina ratio of 65 wt %/35 wt % (see Table 5).

Next, it is described below how to evaluate the performance of the FeGaAl-MFI zeolite (Si/(Fe+Ga+Al)=31.3)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. Table 6 shows the results of the present sample after 5 hours from the start of the reaction.

Example 6

It is described below how to prepare a FeGaAl-MFI zeolite (Si/(Fe+Ga+Al)=12.0)/alumina composite in Example 6.

Na-type FeAl-MFI zeolite was synthesized in the same manner as in Example 1, except that a solution composed of 58.9 g of colloidal silica (30.6 wt % of $SiO_2$, 0.4 wt % of $Na_2O$, and 69.0 wt % of $H_2O$) and 3.98 g of sodium hydroxide was used instead as the liquid A and that a solution composed of 2.54 g of aluminum sulfate n-hydrate, 1.46 g of gallium nitrate n-hydrate, 3.26 g of iron nitrate 9-hydrate, 15.49 g of tetrapropylammonium bromide, and 185.1 g of water was used instead as the liquid B.

In addition, the resultant powdery Na-type FeGaAl-MFI zeolite and alumina powder were used and molded in the same way as in Example 4, so that a cylindrical FeGaAl-MFI zeolite/alumina composite was obtained. The composite was then subjected to ion-exchange to prepare a FeGaAl-MFI zeolite/alumina composite catalyst.

The ion-exchange was performed in the same way as in Example 1. The resultant FeGaAl-MFI zeolite had the following molar ratios of elements: Si/(Fe+Ga+Al)=12.0, Fe/(Fe+Ga+Al)=0.4, Ga/(Fe+Ga+Al)=0.3, and Al/(Fe+Ga+Al)=0.3, and an average particle size of 0.57 μm, and the weight composition of the composite catalyst was zeolite/alumina ratio of 65 wt %/35 wt % (see Table 5).

Next, it is described below how to evaluate the performance of the FeGaAl-MFI zeolite (Si/(Fe+Ga+Al)=12.0)/alumina composite catalyst.

The cylindrical FeGaAl-MFI zeolite/alumina composite prepared according to the above procedure was sized and used as a catalyst sample for performance evaluation, and a reaction test was performed in the same way as in Example 1 except that the reaction time was changed to 24 hours. Table 6 shows the results of the present sample after 5 hours from the start of the reaction. In addition, FIG. 1 shows the time courses of the conversion in the reaction test for 24 hours.

Comparative Example 3

It is described below how to prepare a FeGaAl-MFI zeolite (Si/(Fe+Ga+Al)=50.1)/alumina composite in Comparative Example 3.

Na-type FeAl-MFI zeolite was synthesized in the same manner as in Example 1, except that a solution composed of 58.9 g of colloidal silica (30.6 wt % of $SiO_2$, 0.4 wt % of $Na_2O$, and 69.0 wt % of $H_2O$) and 2.00 g of sodium hydroxide was used instead as the liquid A and that a solution composed of 0.51 g of aluminum sulfate n-hydrate, 0.29 g of gallium nitrate n-hydrate, 0.65 g of iron nitrate 9-hydrate, 3.10 g of tetrapropylammonium bromide, and 187.5 g of water was used instead as the liquid B.

In addition, the resultant powdery Na-type FeGaAl-MFI zeolite and alumina powder were used and molded in the same way as in Example 4, so that a cylindrical FeGaAl-MFI zeolite/alumina composite was obtained.

The composite was then subjected to ion-exchange to prepare a FeGaAl-MFI zeolite/alumina composite catalyst.

The ion-exchange was performed in the same way as in Example 1. The resultant FeGaAl-MFI zeolite had the following molar ratios of elements: Si/(Fe+Ga+Al)=50.1, Fe/(Fe+Ga+Al)=0.4, Ga/(Fe+Ga+Al)=0.3, and Al/(Fe+Ga+Al)=0.3, and an average particle size of 0.90 μm, and the weight composition of the composite catalyst was zeolite/alumina ratio of 65 wt %/35 wt % (see Table 5).

Next, it is described below how to evaluate the performance of the FeGaAl-MFI zeolite (Si/(Fe+Ga+Al)=50.1)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. Table 6 shows the results of the present sample after 5 hours from the start of the reaction.

Comparative Example 4

Next, it is described below how to prepare a micro-sized FeGaAl-MFI zeolite (Si/(Fe+Ga+Al)=12.0 (acid density))/alumina composite.

Liquids A and B were prepared, in which the liquid A was a solution composed of 58.9 g of colloidal silica (30.6 wt % of $SiO_2$, 0.4 wt % of $Na_2O$, and 69.0 wt % of $H_2O$) and 3.98 g of sodium hydroxide, and the liquid B was a solution composed of 2.54 g of aluminum sulfate n-hydrate, 1.46 g of gallium nitrate n-hydrate, 3.26 g of iron nitrate 9-hydrate, 30.98 g of tetrapropylammonium bromide, and 185.1 g of water. The liquids A and B were gradually mixed by stirring at room temperature, and the mixture was then further vigorously stirred for 15 minutes in a mixer. Immediately after the stirring, the mixture was subjected to a hydrothermal synthesis reaction at its own pressure in an autoclave under the conditions of 180° C., 24 hours, and 150 rpm. After cooled, the product was thoroughly washed with purified water (the solid and the aqueous solution were separated using a centrifuge).

Subsequently, the product was dried at 120° C. for 3 hours and then calcined at 550° C. for 3 hours in an air stream, so that Na-type FeGaAl-MFI zeolite containing Fe, Ga, and Al was synthesized. The average particle size of secondary particles of the zeolite was measured by a laser scattering/diffraction analyzer.

In addition, the resultant powdery Na-type FeGaAl-MFI zeolite and alumina powder were used and molded in the same way as in Example 4, so that a cylindrical FeGaAl-MFI zeolite/alumina composite was obtained. The composite was then subjected to ion-exchange to prepare a FeGaAl-MFI zeolite/alumina composite catalyst.

The ion-exchange was performed in the same way as in Example 1. The resultant FeGaAl-MFI zeolite had the following molar ratios of elements: Si/(Fe+Ga+Al)=11.8, Fe/(Fe+Ga+Al)=0.4, Ga/(Fe+Ga+Al)=0.3, and Al/(Fe+Ga+Al)=0.3, and an average particle size of 6.3 μm, and the weight composition of the composite catalyst was zeolite/alumina ratio of 65 wt %/35 wt % (see Table 7).

Next, it is described below how to evaluate the performance of the micro-sized FeGaAl-MFI zeolite (Si/(Fe+Ga+Al)=12.0)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. FIG. 1 shows the time courses of the conversion in reaction test for 5 hours.

Table 6 shows the performance of the composite catalysts, consisting of zeolites with different acid densities (Si/(Fe+Ga+Al)=12.0, 31.3, 50.1 with the Fe/Ga/Al ratio fixed at 0.4/0.3/0.3) (Examples 5 and 6 and Comparative Example 3) and alumina, in comparison with that of the FeGaAl-MFI zeolite/alumina composite catalyst of Example 4 as a reference sample (in which the zeolite has the following molar ratios of elements: Si/(Fe+Ga+Al)=19.4 (acid density), Fe/(Fe+Ga+Al)=0.4, Ga/(Fe+Ga+Al)=0.3, and Al/(Fe+Ga+Al)=0.3, and the weight composition of the composite catalyst is zeolite/alumina ratio of 65 wt %/35 wt %).

When the molar ratios of Si/(Fe+Ga+Al) were in the range from 12.0 to 31.3, higher propylene yields than 20 wt % were obtained (Examples 4 to 6), and the propylene yield reached as high as 31.2 wt % when the sample with a Si/(Fe+Ga+Al) ratio of 12.0 was used.

It was impossible to synthesize MFI-type zeolites with Si/(Fe+Ga+Al) ratios of below 12.0 in the synthesis procedure shown in the examples of the present invention. When a catalyst sample with a Si/(Fe+Ga+Al) ratio of 50.1 was used, the n-hexane conversion and the propylene yield were reduced to ca. 37 wt % and ca. 15 wt %, respectively, due to the small amount of acid sites. It has been thus found that high propylene yields can be obtained when the Si/(Fe+Ga+Al) ratios of FeGaAl-MFI zeolites are in the range from ca. 12.0 to ca. 31.3.

In Examples 1, 2, 5, and 6, these zeolites were in the form of fine zeolite particles in which secondary particles have average sizes of below 1.0 μm. In Example 6, the FeGaAl-MFI zeolite had an average size of ca. 570 nm (see Table 7). When the reaction test was performed for a long time period using this sample, the catalytic performance was maintained for 24 hours at least (see FIG. 1).

On the other hand, as shown in Table 7, coarse zeolite with a micro-order particle size (6.3 μm) and the almost same compositions as that of the fine zeolite was prepared by different synthesis conditions. When such coarse zeolite was used, it was observed that although the initial conversions were almost the same level as those for the fine zeolite (Example 6), the performance sharply decreased in several hours (see FIG. 1). It has been found that fine zeolite particles increase the number of effectively working micropores for cracking reactions, so that the zeolites can be highly resistant to degradation due to coke formation or accumulation.

Next, a second example of the present invention is described below.

The second example corresponds to the second embodiment described above, according to which zeolite catalysts of Examples 1 to 3 shown in Tables 8 and 9 below were experimentally produced, while a zeolite catalyst of Comparative Example 1 was experimentally produced, and lower olefins were produced using the zeolite catalysts of Examples 1 to 3 and Comparative Example 1, respectively. Example 1 provides a zeolite catalyst containing iron atoms but not containing gallium atoms according to the second embodiment, and Example 2 provides a zeolite catalyst containing both iron atoms and gallium atoms according to the second embodiment. Example 3 provides a zeolite catalyst that is produced according to the second embodiment using gallium-loaded alumina as a binder and MFI-type crystalline aluminosilicate containing iron atoms but not containing gallium atoms.

TABLE 8

Listing of compositions of different types of zeolite/Al$_2$O$_3$ composite catalysts

|  | Comparative Example 1 | Example 1 | Example 2 | Example 3 |
|---|---|---|---|---|
| Zeolite species | Al-MFI | FeAl-MFI | FeGaAl-MFI | FeAl-MFI |
| Acid density (Si/(Fe + Ga + Al)) [mol/mol] | 30.7 | 30.5 | 31.3 | 44.7* |
| Molar ratio of Fe (Fe/(Fe + Ga + Al)) | 0.0 | 0.5 | 0.4 | 0.57* |
| Molar ratio of Ga (Ga/(Fe + Ga + Al)) | 0.0 | 0.0 | 0.3 | 0.0* |
| Molar ratio of Al (Al/(Fe + Ga + Al)) | 1.0 | 0.5 | 0.3 | 0.43* |
| Binder type used for molding | Al$_2$O$_3$ powder | Al$_2$O$_3$ powder | Al$_2$O$_3$ Powder | Ga-loaded* Al$_2$O$_3$ powder |
| Mixed ratio of zeolite/binder [wt %/wt %] | 65/35 | 65/35 | 65/35 | 65/35 |

*The total moles of Fe, Ga, and Al in the MFI-zeolite of Example 2 are almost equal to the sum of the total moles of Fe and Al in the MFI-zeolite of Example 3 and the moles of Ga in the Al$_2$O$_3$ binder.

TABLE 9

Comparison of initial performance after 1.5 h from the start of reaction of different zeolite/Al$_2$O$_3$ composite catalysts

|  | Comparative Example 1 | Example 1 | Example 2 | Example 3 |
|---|---|---|---|---|
| Zeolite species | Al-MFI | FeAl-MFI | FeGaAl-MFI | FeAl-MFI |
| Acid density (Si/(Fe + Ga + Al)) | 30.7 | 30.5 | 31.3 | 44.7 |
| Mixed ratio of zeolite/binder [wt %/wt %] | 65/35 | 65/35 | 65/35 | 65/35 |
| Reaction temperature [° C.] | 550 | 550 | 550 | 550 |
| LHSV (based on n-hexane) [h$^{-1}$]/ the charged amount of catalyst [mL] | 2.0/1.0 | 2.0/1.0 | 2.0/1.0 | 2.0/1.0 |
| Total pressure [MPa] | 0.1 | 0.1 | 0.1 | 0.1 |
| Mixed ratio of H$_2$O/n-hexane [mol/mol] | 5/1 | 5/1 | 5/1 | 5/1 |
| n-hexane conversion [wt %] | 69.1 | 68.5 | 77.7 (46.1*) | 77.4 |
| Ethylene yield [wt %] | 12.0 | 9.1 | 11.4 (3.7*) | 10.6 |
| Propylene yield [wt %] | 15.9 | 18.0 | 20.9 (20.0*) | 21.3 |
| Yield of aromatic hydrocarbons [wt %] | 1.5 | 1.6 | 1.4 (2.1*) | 1.7 |
| Space time yield of propylene [g-C$_3$H$_6$/g-zeolite · h] | 0.59 | 0.67 | 0.78 (0.37*) | 0.79 |

*Experimental data obtained in the cracking of n-hexane diluted with nitrogen using the same catalyst (reaction temperature 550° C., the charged amount of catalyst 1.0 mL, LHSV (based on n-hexane) 1.0 h$^{-1}$, total pressure 0.1 MPa, mixed molar ratio of N$_2$/n-hexane 15/1)

The each catalyst of Examples 1 to 3 is in the form of composite combined with an Al$_2$O$_3$ binder. The total moles of iron atoms, gallium atoms, and aluminum atoms in the MFI zeolite of Example 2 are almost equal to the sum of the total moles of iron atoms and aluminum atoms (not including the aluminum atoms in the Al$_2$O$_3$ binder) in the MFI zeolite of Example 3 and the moles of gallium atoms in the Al$_2$O$_3$ binder of Example 3.

Comparative Example 1 provides MFI-type crystalline aluminosilicate free of both iron atoms and gallium atoms (e.g., ZSM-5, which is Al-MFI-type zeolite).

Hereinafter, each example and a comparative example are described below.

Example 1

It is described below how to synthesize FeAl-MFI zeolite in Example 1.

Liquids A and B were prepared, in which the liquid A was a solution composed of 58.9 g of colloidal silica (30.6 wt % of SiO$_2$, 0.4 wt % of Na$_2$O, and 69.0 wt % of H$_2$O) and 2.25 g of sodium hydroxide, and the liquid B was a solution composed of 1.14 g of aluminum sulfate n-hydrate, 0.98 g of iron nitrate 9-hydrate, 4.65 g of tetrapropylammonium bromide, and 187.1 g of water.

The liquids A and B were gradually mixed by stirring at room temperature, and the mixture was then further vigorously stirred for 15 minutes in a mixer. The mixture solution was allowed to stand overnight while its temperature was kept at 60° C. Subsequently, the mixture solution was subjected to a hydrothermal synthesis reaction at its own pressure in an autoclave under the conditions of 150° C., 24 hours, and 300 rpm. After cooled, the product was thoroughly washed with purified water (the solid and the aqueous solution were separated using a centrifuge).

Subsequently, the product was dried at 120° C. for 3 hours and then calcined at 550° C. for 3 hours in an air stream, so that powdery Na-type-MFI zeolite containing iron and aluminum atoms (hereinafter abbreviated as FeAl-MFI zeolite) was synthesized. The zeolite had the following molar rations of elements: Si/(Fe+Al)=30.5, Fe/(Fe+Al)=0.5, and Al/(Fe+Al)=0.5 (see Table 8).

Next, it is described below how to prepare a FeAl-MFI zeolite/alumina composite catalyst.

The powdery Na-type FeAl-MFI zeolite (4.0 wt % in water content) synthesized according to the above procedure and alumina powder (Cataloid AP-1, 71.7 wt % in Al$_2$O$_3$ content, JGC Catalysts and Chemicals Ltd.) were kneaded while a proper amount of purified water was added to them, so that a massive zeolite/alumina mixture was obtained. The mixture was then formed into a cylindrical product (1.0 mmφ) using an extruder. The product was dried at 120° C.

for 3 hours and then calcined at 550° C. for 3 hours in an air stream, so that a FeAl-MFI zeolite/alumina composite was obtained.

The composite was subjected to ion exchange using a 2.2 mol/L ammonium nitrate aqueous solution under boiling and refluxing conditions, and then washed with purified water. This process was repeated four times (in which each ion exchange was performed for 2 hours, and the 2.2 mol/L ammonium nitrate aqueous solution was replaced with new one every time). Subsequently, the product was dried at 120° C. for 3 hours and then calcined at 550° C. for 3 hours in an air stream to give a proton-type FeAl-MFI zeolite/alumina composite catalyst. The weight composition of the composite catalyst was zeolite/alumina ratio of 65 wt %/35 wt % (see Table 8).

Next, it is described below how to evaluate the performance of the FeAl-MFI zeolite/alumina composite catalyst.

The cylindrical FeAl-MFI zeolite/alumina composite prepared according to the above procedure was sized and used as a catalyst sample for performance evaluation. Catalytic cracking of n-hexane was carried out in a fixed-bed-type reactor in order to evaluate catalytic performance of this composite zeolite. The catalyst of 1.0 mL was charged into a stainless-steel tubular reactor (made of SUS 316) with an inner diameter of 8.0 mm in such a manner that a catalyst layer with height of ca. 20 mm was formed. Glass wool was packed before and after the catalyst layer, and glass beads were charged before and after the glass wool.

The catalytic cracking reaction of n-hexane was performed for 5 hours under the reaction conditions of: a reaction temperature of 550° C.; a total pressure of 0.1 MPa; a n-hexane flow rate of 1.31 g/h (liquid hourly space velocity (LHSV) based on n-hexane: 2.0 h$^{-1}$); and a purified water flow rate of 1.37 g/h (H$_2$O/n-hexane=5 mol/mol) in the presence of steam. The reaction products were examined by gas-chromatographic analysis at regular intervals, in which the feedstock (n-hexane) conversion (wt %), the yield (wt %) of lower olefins (ethylene and propylene), and the yield (wt %) of aromatic hydrocarbons were determined as factors exhibiting catalytic performance. Table 9 shows the results of the present sample after 1.5 hours from the start of the reaction, and FIG. 2 shows the time courses of the n-hexane conversion.

Example 2

It is described below how to synthesize FeGaAl-MFI zeolite in Example 2.

Powdery Na-type FeGaAl-MFI zeolite was synthesized in the same manner as in Example 1, except that a solution composed of 0.76 g of aluminum sulfate n-hydrate, 0.44 g of gallium nitrate n-hydrate, 0.98 g of iron nitrate 9-hydrate, 4.65 g of tetrapropylammonium bromide, and 187.2 g of water was used instead as the liquid B.

The resultant FeGaAl-MFI zeolite had the following molar ratios of elements: Si/(Fe+Ga+Al)=31.3 (acid density), Fe/(Fe+Ga+Al)=0.4, Ga/(Fe+Ga+Al)=0.3, and Al/(Fe+Ga+Al)=0.3 (see Table 8).

Next, it is described below how to prepare a FeGaAl-MFI zeolite/alumina composite catalyst.

The powdery Na-type FeGaAl-MFI zeolite synthesized according to the above procedure and alumina powder were used and subjected to molding and ion exchange in the same manner as in Example 1, so that a cylindrical proton-type FeGaAl-MFI zeolite/alumina composite catalyst was obtained. The weight composition of the composite catalyst was zeolite/alumina ratio of 65 wt %/35 wt % (see Table 8).

Next, it is described below how to evaluate the performance of the FeGaAl-MFI zeolite/alumina composite catalyst. The cylindrical FeGaAl-MFI zeolite/alumina composite prepared according to the above procedure was sized and used as a catalyst sample for performance evaluation, and a reaction test was performed in the same way as in Example 1. Table 9 shows the results of the present sample after 1.5 hours from the start of the reaction, and FIG. 2 shows the time courses of the n-hexane conversion.

Example 3

It is described below how to synthesize FeAl-MFI zeolite in Example 3.

Powdery Na-type FeAl-MFI zeolite was synthesized in the same manner as in Example 1, except that a solution composed of 0.76 g of aluminum sulfate n-hydrate, 0.98 g of iron nitrate 9-hydrate, 3.26 g of tetrapropylammonium bromide, and 187.2 g of water was used instead as the liquid B.

The resultant FeAl-MFI zeolite had the following molar ratios of elements: Si/(Fe+Al)=44.7 (acid density), Fe/(Fe+Al)=0.57, and Al/(Fe+Al)=0.43 (see Table 8).

Next, it is described below how to prepare a FeAl-MFI zeolite/gallium-loaded alumina composite catalyst.

The powdery Na-type FeAl-MFI zeolite synthesized according to the above procedure and alumina powder on which gallium had been loaded in advance were used and subjected to molding and ion-exchange in the same manner as in Example 1, so that a cylindrical proton-type FeAl-MFI zeolite/gallium-containing alumina composite catalyst was obtained. Here the gallium content contained in the Al$_2$O$_3$ binder of Example 3 was the same as the content of Ga in the FeGaAl-MFI zeolite of Example 2. Therefore, the sum of the total moles of Fe and Al atoms in the zeolite of this example and the moles of Ga atoms in the alumina binder of this example was almost equal to the total moles of Fe, Ga, and Al atoms in the zeolite component of Example 2.

The weight composition of the composite catalyst was zeolite/alumina ratio of 65 wt %/35 wt % (see Table 8).

Next, it is described below how to evaluate the performance of the FeAl-MFI zeolite/gallium-containing alumina composite catalyst.

The cylindrical FeAl-MFI zeolite/gallium-containing alumina composite prepared according to the above procedure was sized and used as a catalyst sample for performance evaluation, and a reaction test was performed in the same way as in Example 1. Table 9 shows the results of the present sample after 1.5 hours from the start of the reaction, and FIG. 2 shows the time courses of the n-hexane conversion.

Comparative Example 1

It is described below how to synthesize Al-MFI zeolite in Comparative Example 1.

Na-type Al-MFI zeolite was synthesized in the same manner as in Example 1, except that a solution composed of 1.90 g of aluminum sulfate n-hydrate, 4.65 g of tetrapropylammonium bromide, and 187.2 g of water was used instead as the liquid B. The resultant Al-MFI zeolite had the element mole ratio: Si/Al=30.7 (see Table 8).

Next, it is described below how to prepare an Al-MFI zeolite/alumina composite catalyst.

The powdery Na-type Al-MFI zeolite synthesized according to the above procedure and alumina powder were used and subjected to molding and ion-exchange in the same manner as in Example 1, so that a cylindrical proton-type Al-MFI zeolite/alumina composite catalyst was obtained.

The weight composition of the composite catalyst was zeolite/alumina ratio of 65 wt %/35 wt % (see Table 8).

Next, it is described below how to evaluate the performance of the Al-MFI zeolite/alumina composite catalyst.

The cylindrical Al-MFI zeolite/alumina composite prepared according to the above procedure was sized and used as a catalyst sample for performance evaluation, and a reaction test was performed in the same way as in Example 1. Table 9 shows the results of the present sample after 1.5 hours from the start of the reaction, and FIG. 2 shows the time courses of the n-hexane conversion.

Next, the experimental results shown in Table 9 and FIG. 2 are explained below.

When conventional Al-MFI zeolite (Comparative Example 1) was used, formation of aromatic hydrocarbons was suppressed in the presence of steam as shown in Table 9, but as is evident from the time courses in FIG. 2, degradation of the catalyst was observed in several hours, and the catalyst was found to be not stable under the existence of steam. Because the yield of aromatic hydrocarbons was reduced to less than 2 wt %, it is suggested that this degradation was more likely to occur due to destruction of zeolite structure derived from dealumination under steam atmosphere than coke formation.

On the other hand, it has been observed that the use of FeAl-MFI zeolite containing iron atoms having the effect of reducing acid strength (Example 1) or the use of FeGaAl-MFI zeolite containing both iron atoms having the effect of reducing acid strength and gallium atoms having the effect of accelerating alkane dehydrogenation (Examples 2 and 3) makes it possible not only to improve the propylene yield but also to keep the stable performance even under steam (see FIG. 2).

When the sample of Example 2 was used, the space time yield of propylene was ca. 0.78 (g-$C_3H_6$/g-zeolite·h), being ca. twice of that obtained in the case of testing this sample in the presence of nitrogen. In the present invention, the space time yield of propylene (g-$C_3H_6$/g-zeolite·h) was defined as the weight of propylene that can be produced per hour by zeolite of one gram. Since optimal feed-rate of feedstock depends on the kind of diluent, the space time yield of propylene was adopted as a factor for comparing catalytic performance incases of using different diluents. Furthermore, as shown in the comparison of Examples 2 and 3 (see Table 9), it was found that either the use of gallium contained in zeolite or the use of gallium contained in a binder was almost equally effective in improving the propylene yield and stability.

Next, a third example of the present invention is described below.

The third example corresponds to the third embodiment described above, according to which zeolite catalysts of Examples 1 to 4 shown in Tables 10 and 11 below were experimentally produced, while zeolite catalysts of Comparative Examples 1 and 2 were experimentally produced, and lower olefins were produced using the produced zeolite catalysts of Examples 1 to 4 and Comparative Examples 1 and 2, respectively. Examples 1 to 3 provide zeolite catalysts containing both iron atoms and gallium atoms according to the above embodiment, in which different acid densities are set, respectively, as shown in Tables 10 and 11.

TABLE 10

Listing of compositions of FeGaAl-MFI/$Al_2O_3$ composite catalysts with different acid densities

|  | Comparative Example 1 | Comparative Example 2 | Example 1 | Example 2 | Example 3 | Example 4 |
| --- | --- | --- | --- | --- | --- | --- |
| Zeolite species | FeGaAl-MFI | FeGaAl-MFI | FeGaAl-MFI | FeGaAl-MFI | FeGaAl-MFI | FeAl-MFI |
| Acid density (Si/(Fe + Ga + Al)) [mol/mol] | 19.4 | 472.7 | 92.9 | 121.3 | 177.5 | 123.1 |
| Fe mole ratio (Fe/(Fe + Ga + Al)) | 0.4 | 0.4 | 0.4 | 0.4 | 0.4 | 0.5 |
| Ga mole ratio (Ga/(Fe + Ga + Al)) | 0.3 | 0.3 | 0.3 | 0.3 | 0.3 | 0.0 |
| Al mole ratio (Al/(Fe + Ga + Al)) | 0.3 | 0.3 | 0.3 | 0.3 | 0.3 | 0.5 |
| Binder type used for molding | $Al_2O_3$ powder | $Al_2O_3$ powder | $Al_2O_3$ powder | $Al_2O_3$ powder | $Al_2O_3$ powder | $Al_2O_3$ powder |
| Mixed ratio of zeolite/binder [wt %/wt %] | 65/35 | 65/35 | 65/35 | 65/35 | 65/35 | 65/35 |

TABLE 11

Comparison of the performance of FeGaAl-MFI/$Al_2O_3$ composite catalysts with different acid densities

|  | Comparative Example 1 | Comparative Example 2 | Example 1 | Example 2 | Example 3 | Example 4 |
| --- | --- | --- | --- | --- | --- | --- |
| Zeolite species | FeGaAl-MFI | FeGaAl-MFI | FeGaAl-MFI | FeGaAl-MFI | FeGaAl-MFI | FeAl-MFI |
| Acid density (Si/(Fe + Ga + Al)) | 19.4 | 472.7 | 92.9 | 121.3 | 177.5 | 123.1 |
| Mixed ratio of zeolite/binder [wt %/wt %] | 65/35 | 65/35 | 65/35 | 65/35 | 65/35 | 65/35 |

TABLE 11-continued

Comparison of the performance of FeGaAl-MFI/Al$_2$O$_3$ composite catalysts with different acid densities

| | Comparative Example 1 | Comparative Example 2 | Example 1 | Example 2 | Example 3 | Example 4 |
|---|---|---|---|---|---|---|
| Reaction temperature [° C.] | 565 | 565 | 565 | 565 | 565 | 565 |
| Charged amount of catalyst [mL] | 2.0 | 2.0 | 2.0 | 2.0 | 2.0 | 2.0 |
| LHSV (based on n-hexane) [h$^{-1}$] | 5.0 | 5.0 | 5.0 | 5.0 | 5.0 | 5.0 |
| Total pressure [MPa] | 0.1 | 0.1 | 0.1 | 0.1 | 0.1 | 0.1 |
| n-hexane conversion [wt %] | 81.4 (80.9*) | 39.5 | 66.9 | 67.3 | 61.6 | 67.8 |
| Ethylene yield [wt %] | 5.4 (10.0*) | 3.2 | 8.0 | 8.2 | 6.6 | 8.2 |
| Propylene yield [wt %] | 10.6 (28.3*) | 8.7 | 16.8 | 18.1 | 15.5 | 17.0 |
| Aromatics yield [wt %] | 19.4 (10.8*) | 3.2 | 7.5 | 7.3 | 4.8 | 5.4 |
| Space time yield of propylene [g-C$_3$H$_6$/g-zeolite · h] | 0.65 (0.53*) | 0.53 | 1.0 | 1.1 | 0.95 | 1.0 |

*Experimental data obtained in the cracking of n-hexane diluted with nitrogen using the same catalyst (reaction temperature 550° C., the charged amount of catalyst 1.0 mL, LHSV (based on n-hexane) 1.0 h$^{-1}$, total pressure 0.1 MPa, N$_2$/n-hexane mixing molar ratio 15/1)

Example 4 provides a zeolite catalyst containing iron atoms but not containing gallium atoms according to the above embodiment.

In Comparative Example 1, the Si/(Fe+Ga+Al) ratio is less than 75.0. Therefore, the acid density in Comparative Example 1 is higher than those in Examples 1 to 4. In Comparative Example 2, the Si/(Fe+Ga+Al) ratio is more than 200.0. Therefore, the acid density in Comparative Example 2 is lower than those in Examples 1 to 4.

Hereinafter, each example and each comparative example are described below.

Example 1

It is described below how to synthesize FeGaAl-MFI zeolite (Si/(Fe+Ga+Al)=92.9 (acid density)) in Example 1.

Liquids A and B were prepared, in which the liquid A was a solution composed of 58.9 g of colloidal silica (30.6 wt % of SiO$_2$, 0.4 wt % of Na$_2$O, and 69.0 wt % of H$_2$O) and 1.76 g of sodium hydroxide, and the liquid B was a solution composed of 0.25 g of aluminum sulfate n-hydrate, 0.15 g of gallium nitrate n-hydrate, 0.33 g of iron nitrate 9-hydrate, 4.13 g of tetrapropylammonium bromide, and 187.8 g of purified water. The liquids A and B were gradually mixed by stirring at room temperature, and the mixture was then further vigorously stirred for 15 minutes in a mixer.

The mixture solution was allowed to stand overnight while its temperature was kept at 60° C. Subsequently, the mixture solution was subjected to a hydrothermal synthesis reaction at its own pressure in an autoclave under the conditions of 150° C., 72 hours, and 300 rpm.

After cooled, the product was thoroughly washed with purified water (the solid and the aqueous solution were separated using a centrifuge).

Subsequently, the product was dried at 120° C. for 3 hours and then calcined at 550° C. for 3 hours in an air stream, so that powdery Na-type-MFI zeolite containing iron, gallium, and aluminum atoms (hereinafter abbreviated as FeGaAl-MFI zeolite) was synthesized. The zeolite had the following molar ratios of elements: Si/(Fe+Ga+Al)=92.9 (acid density), Fe/(Fe+Ga+Al)=0.4, Ga/(Fe+Ga+Al)=0.3, and Al/(Fe+Ga+Al)=0.3 (see Table 10).

Next, it is described below how to prepare a FeGaAl-MFI zeolite (Si/(Fe+Ga+Al)=92.9)/alumina composite catalyst.

The powdery Na-type FeGaAl-MFI zeolite (4.0 wt % in water content) synthesized according to the above procedure and alumina powder (Cataloid AP-1, 71.7 wt % in Al$_2$O$_3$ content, JGC Catalysts and Chemicals Ltd.) were kneaded while a proper amount of purified water was added to them, so that a massive zeolite/alumina mixture was obtained. The mixture was then formed into a cylindrical product (1.0 mmφ) using an extruder. The product was dried at 120° C. for 3 hours and then calcined at 550° C. for 3 hours in an air stream, so that a FeGaAl-MFI zeolite/alumina composite was obtained.

The composite was subjected to ion exchange using a 2.2 mol/L ammonium nitrate aqueous solution under boiling reflux, and then washed with purified water. This process was repeated four times (in which each ion exchange was performed for 2 hours, and the 2.2 mol/L ammonium nitrate aqueous solution was replaced with new one every time). Subsequently, the product was dried at 120° C. for 3 hours and then calcined at 550° C. for 3 hours in an air stream to give a proton-type FeGaAl-MFI zeolite/alumina composite catalyst. The weight composition of the composite catalyst was zeolite/alumina ratio of 65 wt %/35 wt % (see Table 10).

Next, it is described below how to evaluate the performance of the FeGaAl-MFI zeolite (Si/(Fe+Ga+Al)=92.9)/alumina composite catalyst.

The cylindrical FeGaAl-MFI zeolite (Si/(Fe+Ga+Al)=92.9)/alumina composite prepared according to the above procedure was sized and used as a catalyst sample for performance evaluation. Catalytic cracking of n-hexane was carried out in a fixed-bed-type reactor in order to evaluate catalytic performance of this composite zeolite.

The catalyst of 2.0 mL was charged into a stainless-steel tubular reactor (made of SUS 316) with an inner diameter of 12.575 mm in such a manner that a catalyst layer with height of ca. 20 mm was formed. Glass wool was packed before and after the catalyst layer, and glass beads were charged before and after the glass wool. The catalytic cracking reaction of n-hexane was performed for 24 hours under the reaction conditions of: a reaction temperature of 565° C.; a total pressure of 0.1 MPa; and an n-hexane flow rate of 6.5 g/h (liquid hourly space velocity (LHSV) based on n-hexane: 5.0 h$^{-1}$). The reaction products were examined by gas-chromatographic analysis after 24 hours from the start of the reaction. In the analysis, feedstock (n-hexane) conversion (wt %), the yield (wt %) of lower olefins (ethylene and propylene), and the yield (wt %) of aromatic hydrocarbons were determined as factors exhibiting catalyst performance. Table 11 shows the results of the present sample after 24 hours from the start of the reaction.

Example 2

It is described below how to synthesize FeGaAl-MFI zeolite (Si/(Fe+Ga+Al)=121.3 (acid density)) in Example 2.

Na-type FeGaAl-MFI zeolite was synthesized in the same manner as in Example 1, except that a solution composed of 58.9 g of colloidal silica (30.6 wt % of SiO$_2$, 0.4 wt % of Na$_2$O, and 69.0 wt % of H$_2$O) and 1.69 g of sodium hydroxide was used instead as the liquid A and that a solution composed of 0.19 g of aluminum sulfate n-hydrate, 0.11 g of gallium nitrate n-hydrate, 0.24 g of iron nitrate 9-hydrate, 3.10 g of tetrapropylammonium bromide, and 187.8 g of purified water was used instead as the liquid B.

The resultant FeGaAl-MFI zeolite had the following molar ratio of elements: Si/(Fe+Ga+Al)=121.3 (acid density), Fe/(Fe+Ga+Al)=0.4, Ga/(Fe+Ga+Al)=0.3, and Al/(Fe+Ga+Al)=0.3 (see Table 10).

Next, it is described below how to prepare an FeGaAl-MFI zeolite (Si/(Fe+Ga+Al)=121.3)/alumina composite catalyst.

The powdery Na-type FeGaAl-MFI zeolite (Si/(Fe+Ga+Al)=121.3) synthesized according to the above procedure and alumina powder were used and subjected to molding and ion exchange in the same manner as in Example 1, so that a cylindrical proton-type FeGaAl-MFI zeolite (Si/(Fe+Ga+Al)=121.3) composite catalyst was obtained. The weight composition of the composite catalyst was zeolite/alumina ratio of 65 wt %/35 wt % (see Table 10).

Next, it is described below how to evaluate the performance of the FeGaAl-MFI zeolite (Si/(Fe+Ga+Al)=121.3)/alumina composite catalyst.

The cylindrical FeGaAl-MFI zeolite/alumina composite prepared according to the above procedure was sized and used as a catalyst sample for performance evaluation, and a reaction test was performed in the same way as in Example 1, except that the reaction time was changed to 80 hours. Table 11 shows the results of the present sample after 24 hours from the start of the reaction. FIG. 3 shows the time courses of the conversion, ethylene yield, and propylene yield for 80 hours when the sample was used.

Example 3

It is described below how to synthesize FeGaAl-MFI zeolite (Si/(Fe+Ga+Al)=177.5 (acid density)) in Example 3.

Na-type FeGaAl-MFI zeolite was synthesized in the same manner as in Example 1, except that a solution composed of 58.9 g of colloidal silica (30.6 wt % of SiO$_2$, 0.4 wt % of Na$_2$O, and 69.0 wt % of H$_2$O) and 1.58 g of sodium hydroxide was used instead as the liquid A and that a solution composed of 0.08 g of aluminum sulfate n-hydrate, 0.04 g of gallium nitrate n-hydrate, 0.10 g of iron nitrate 9-hydrate, 2.48 g of tetrapropylammonium bromide, and 188.0 g of purified water was used instead as the liquid B.

The resultant FeGaAl-MFI zeolite had the following molar ratios of elements: Si/(Fe+Ga+Al)=177.5 (acid density), Fe/(Fe+Ga+Al)=0.4, Ga/(Fe+Ga+Al)=0.3, and Al/(Fe+Ga+Al)=0.3 (see Table 10).

Next, it is described below how to prepare an FeGaAl-MFI zeolite (Si/(Fe+Ga+Al)=177.5)/alumina composite catalyst.

The powdery Na-type FeGaAl-MFI zeolite (Si/(Fe+Ga+Al)=177.5) synthesized according to the above procedure and alumina powder were used and subjected to molding and ion-exchange in the same manner as in Example 1, so that a cylindrical proton-type FeGaAl-MFI zeolite (Si/(Fe+Ga+Al)=177.5)/alumina composite catalyst was obtained. The weight composition of the composite catalyst was zeolite/alumina ratio of 65 wt %/35 wt % (see Table 10).

Next, it is described below how to evaluate the performance of the FeGaAl-MFI zeolite (Si/(Fe+Ga+Al)=177.5)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. Table 11 shows the results of the present sample after 24 hours from the start of the reaction.

Example 4

Next, it is described below how to synthesize FeAl-MFI zeolite (Si/(Fe+Al)=123.1 (acid density)) in Example 4.

Na-type FeAl-MFI zeolite was synthesized in the same manner as in Example 1, except that a solution composed of 58.9 g of colloidal silica (30.6 wt % of SiO$_2$, 0.4 wt % of Na$_2$O, and 69.0 wt % of H$_2$O) and 1.69 g of sodium hydroxide was used instead as the liquid A and that a solution composed of 0.29 g of aluminum sulfate n-hydrate, 0.24 g of iron nitrate 9-hydrate, 3.10 g of tetrapropylammonium bromide, and 187.8 g of purified water was used instead as the liquid B.

The resultant FeAl-MFI zeolite had the following molar ratios of elements: Si/(Fe+Al)=121.3 (acid density), Fe/(Fe+Al)=0.5, and Al/(Fe+Al)=0.5 (see Table 10).

Next, it is described below how to prepare a FeAl-MFI zeolite (Si/(Fe+Al)=123.1)/alumina composite catalyst.

The powdery Na-type FeAl-MFI zeolite (Si/(Fe+Al)=123.1) synthesized according to the above procedure and alumina powder were used and subjected to molding and ion-exchange in the same manner as in Example 1, so that a cylindrical proton-type FeAl-MFI zeolite (Si/(Fe+Al)=123.1)/alumina composite catalyst was obtained. The weight composition of the composite catalyst was zeolite/alumina ratio of 65 wt %/35 wt % (see Table 10).

Next, it is described below how to evaluate the performance of the FeAl-MFI zeolite (Si/(Fe+Al)=123.1)/alumina composite catalyst.

The cylindrical FeAl-MFI zeolite/alumina composite prepared according to the above procedure was sized and used as a catalyst sample for performance evaluation, and a reaction test was performed in the same way as in Example 1, except that the reaction time was changed to 50 hours. Table 11 shows the results of the present sample after 24 hours from the start of the reaction. FIG. 3 shows the time courses of the conversion, ethylene yield, and propylene yield for 50 hours when the sample was used.

Comparative Example 1

Next, it is described below how to synthesize FeGaAl-MFI zeolite (Si/(Fe+Ga+Al)=19.4 (acid density)) in Comparative Example 1.

Na-type FeGaAl-MFI zeolite was synthesized in the same manner as in Example 1, except that a solution composed of 58.9 g of colloidal silica (30.6 wt % of $SiO_2$, 0.4 wt % of $Na_2O$, and 69.0 wt % of $H_2O$) and 2.99 g of sodium hydroxide was used instead as the liquid A and that a solution composed of 1.52 g of aluminum sulfate n-hydrate, 0.88 g of gallium nitrate n-hydrate, 1.96 g of iron nitrate 9-hydrate, 9.29 g of tetrapropylammonium bromide, and 186.3 g of purified water was used instead as the liquid B.

The resultant FeGaAl-MFI zeolite had the following molar ratio of elements: Si/(Fe+Ga+Al)=19.4 (acid density), Fe/(Fe+Ga+Al)=0.4, Ga/(Fe+Ga+Al)=0.3, and Al/(Fe+Ga+Al)=0.3 (see Table 10).

Next, it is described below how to prepare a FeGaAl-MFI zeolite (Si/(Fe+Ga+Al)=19.4)/alumina composite catalyst.

The powdery Na-type FeGaAl-MFI zeolite (Si/(Fe+Ga+Al)=19.4) synthesized according to the above procedure and alumina powder were used and subjected to molding and ion exchange in the same manner as in Example 1, so that a cylindrical proton-type FeGaAl-MFI zeolite (Si/(Fe+Ga+Al)=19.4)/alumina composite catalyst was obtained. The weight composition of the composite catalyst was zeolite/alumina ratio of 65 wt %/35 wt % (see Table 10).

Next, it is described below how to evaluate the performance of the FeGaAl-MFI zeolite (Si/(Fe+Ga+Al)=19.4)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. Table 11 shows the results of the present sample after 24 hours from the start of the reaction.

Comparative Example 2

Next, it is described below how to synthesize FeGaAl-MFI zeolite (Si/(Fe+Ga+Al)=472.7 (acid density)) in Comparative Example 2.

Na-type FeGaAl-MFI zeolite was synthesized in the same manner as in Example 1, except that a solution composed of 18.39 g of fumed silica (Aerosil 200, 98.0 wt % of $SiO_2$ and 2.0 wt % of $H_2O$), 1.93 g of sodium hydroxide, and 114.1 g of purified water was used instead as the liquid A and that a solution composed of 0.08 g of aluminum sulfate n-hydrate, 0.04 g of gallium nitrate n-hydrate, 0.10 g of iron nitrate 9-hydrate, 2.48 g of tetrapropylammonium bromide, and 114.1 g of purified water was used instead as the liquid B.

The resultant FeGaAl-MFI zeolite had the following molar ratios of elements: Si/(Fe+Ga+Al)=472.7, Fe/(Fe+Ga+Al)=0.4, Ga/(Fe+Ga+Al)=0.3, and Al/(Fe+Ga+Al)=0.3 (see Table 10).

Next, it is described below how to prepare a FeGaAl-MFI zeolite (Si/(Fe+Ga+Al)=472.7)/alumina composite catalyst.

The powdery Na-type FeGaAl-MFI zeolite (Si/(Fe+Ga+Al)=472.7) synthesized according to the above procedure and alumina powder were used and subjected to molding and ion exchange in the same manner as in Example 1, so that a cylindrical proton-type FeGaAl-MFI zeolite (Si/(Fe+Ga+Al)=472.7)/alumina composite catalyst was obtained. The weight composition of the composite catalyst was zeolite/alumina ratio of 65 wt %/35 wt % (see Table 10).

Next, it is described below how to evaluate the performance of the FeGaAl-MFI zeolite (Si/(Fe+Ga+Al)=472.7)/alumina composite catalyst.

The cylindrical FeGaAl-MFI zeolite/alumina composite prepared according to the above procedure was sized and used as a catalyst sample for performance evaluation, and a reaction test was performed in the same way as in Example 1. Table 11 shows the results of the present sample after 24 hours from the start of the reaction.

The experimental results in Examples 1 to 4 and Comparative Examples 1 and 2 described above are explained below.

It was found that a composite catalyst of alumina and FeGaAl-MFI zeolite with high acid density (molar ratios of elements: Si/(Fe+Ga+Al)=19.4, Fe/(Fe+Ga+Al)=0.4, Ga/(Fe+Ga+Al)=0.3, Al/(Fe+Ga+Al)=0.3) (Comparative Example 1) gave high propylene-yield from n-hexane feedstock diluted with nitrogen (see Table 11), but in the case of reaction test using n-hexane without dilution according to the present invention, the propylene yield was reduced to less than half of that in the case of testing this sample in the presence of nitrogen (see Table 11), and formation of aromatic hydrocarbons proceeded dominantly.

On the other hand, when composite catalysts of alumina and FeGaAl-MFI zeolite with low acid densities (Si/(Fe+Ga+Al)=92.9, 121.3, and 177.5, the Fe/Ga/Al ratio is fixed at 0.4/0.3/0.3) were used (Examples 1 to 3), these catalysts enhanced the selectivity to lower olefins due to the suppression of formation of aromatic hydrocarbons and gave the high yields of propylene (see Table 11), although the feedstock conversion decreased with decreasing acid density.

In the case of the sample of Example 2 (Si/(Fe+Ga+Al)=121.3) was used, the apparent propylene yield was increased to ca. 18 wt %. The space time yield of propylene was ca. 1.1 (g-$C_3H_6$/g-zeolite·h), being ca. twice of that obtained in the case of testing this sample in the presence of nitrogen. In the present invention, the space time yield of propylene (g-$C_3H_6$/g-zeolite·h) was defined as the weight of propylene that can be produced per hour by zeolite of one gram. Since optimal feed-rate of feedstock depends on the presence or absence of diluent, the space time yield of propylene was adopted as a factor for comparing catalytic performance in cases of using feedstock without dilution and feedstock diluted with nitrogen.

It was also found that a composite catalyst (Example 4) of FeAl-MFI zeolite with the same level of acid density as that in Example 2 (Si/(Fe+Al)=123.1) and alumina also exhibited the same level of high propylene yield (see Table 11). When the sample of Comparative Example 2 (Si/(Fe+Ga+Al)=472.7) was used, the feedstock conversion the propylene yield were reduced to 39.5 wt % and 8.7 wt %, respectively, because of the low acid density.

Thus, it has been found that when hydrocarbon feedstock without dilution is employed for catalytic cracking reaction, FeGaAl-MFI zeolite or FeAl-MFI zeolite with low acid densities within a certain range can gave high yields of propylene. When reaction tests were performed for long time using the samples of Examples 2 and 4, providing high yields of propylene, the catalytic performance were maintained for ca. 50-80 hours (see FIG. 1). These results show that these catalysts are highly resistant to degradation due to coke formation or accumulation.

The invention claimed is:

1. A method for producing lower olefins having 2 to 4 carbon atoms from hydrocarbon feedstocks with low boiling points having a range of boiling points from 35° C. to 200° C., the method comprising:

performing reactions to produce the lower olefins from the hydrocarbon feedstocks with low boiling points in the presence of a zeolite catalyst at a reaction temperature in the range of from 525° C. to 575° C., wherein the zeolite catalyst comprises a MFI-type crystalline aluminosilicate containing iron atoms in a skeleton resulting from a hydrothermal synthesis reaction based on an iron source, a silicon source, and an aluminum source, and wherein the zeolite catalyst has a molar ratio of iron atoms to total moles of iron atoms and aluminum atoms in the range of from 0.4 to 0.7.

2. The method according to claim 1, wherein the lower olefins are produced from the hydrocarbon feedstocks with low boiling points which are diluted with at least one of inert gas and steam, and wherein the zeolite catalyst has an acid density, defined as molar ratios of silicon atoms to total moles of iron atoms and aluminum atoms, in the range of from 12.0 to 45.0.

3. The method according to claim 1, wherein the lower olefins are produced from the hydrocarbon feedstocks with low boiling points which are not diluted, and wherein the zeolite catalyst has an acid density, defined as molar ratios of silicon atoms to total moles of iron atoms and aluminum atoms, in the range of from 75.0 to 200.0.

* * * * *